(12) United States Patent
Wei et al.

(10) Patent No.: US 6,670,164 B2
(45) Date of Patent: Dec. 30, 2003

(54) ISOLATED HUMAN KINASE PROTEINS

(75) Inventors: Ming-Hui Wei, Germantown, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/274,978

(22) Filed: Oct. 22, 2002

(65) Prior Publication Data

US 2003/0064475 A1 Apr. 3, 2003

Related U.S. Application Data

(60) Division of application No. 09/858,664, filed on May 17, 2001, now Pat. No. 6,482,624, which is a continuation-in-part of application No. 09/711,134, filed on Nov. 14, 2000, now abandoned.

(51) Int. Cl.[7] ............................ C12N 9/12; C12N 5/00; C12N 15/00; C12N 1/20; C07K 1/00
(52) U.S. Cl. .................... 435/194; 530/350; 435/320.1; 435/325; 435/252.3; 536/23.2
(58) Field of Search .............................. 435/194, 252.3, 435/320.1, 325; 536/23.2; 530/350

(56) References Cited

FOREIGN PATENT DOCUMENTS

JP   0 911 408 A   4/1999

OTHER PUBLICATIONS

Gallagher P.J. et al. "Molecular Characterization of a Mammalian Smooth Muscle Myosin Light Chain Kinase." Journal of Biological Chemistry, American Society of Biological Chemists, Baltimore, MD, US. vol. 266, No. 35. Dec. 15, 1991. pp. 23936–23944. XP000979557.

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

20 Claims, 17 Drawing Sheets

```
   1 CAGCACGAGG AACTCCTTCT GATCACCTGG CCAGCTGAGG TCAGAGTGGG
  51 AGAGGCAGTG GTTCCATTGA AGGAGTACTC CTAACTGTCA GAAGCCTGGG
 101 CGGTCAGGAT GGGGTGCTGT CGCTTGGGCT GCGGGGGGTG TTCAGTTGCC
 151 CACAGTGTAT CTCAGGGTCT CACCAACCAT CCAAGCATGG TAGGCTGTGG
 201 CTGGCACCCA GGGTTGTGTG GCTGGGGAGG TGGTCTCCAC AGTTCCCTCC
 251 CTGCCCTCCC AGGGCCCCCA TCCATGCAGG TAACCATCGA GGATGTGCAG
 301 GCACAGACAG GCGGAACGGC CCAATTCGAG GCTATCATTG AGGGCGACCC
 351 ACAGCCCTCG GTGACCTGGT ACAAGGACAG CGTCCAGCTG GTGGACAGCA
 401 CCCGGCTTAG CCAGCAGCAA GAAGGCACCA CATACTCCCT GGTGCTGAGG
 451 CATGTGGCCT CGAAGGATGC CGGCGTTTAC ACCTGCCTGG CCCAAAACAC
 501 TGGTGGCCAG GTGCTCTGCA AGGCAGAGCT GCTGGTGCTT GGGGGGGACA
 551 ATGAGCCGGA CTCAGAGAAG CAAAGCCACC GGAGGAAGCT GCACTCCTTC
 601 TATGAGGTCA AGGAGGAGAT TGGAAGGGGC GTGTTTGGCT TCGTAAAAAG
 651 AGTGCAGCAC AAAGGAAACA AGATCTTGTG CGCTGCCAAG TTCATCCCCC
 701 TACGGAGCAG AACTCGGGCC CAGGCATACA GGGAGCGAGA CATCCTGGCC
 751 GCGCTGAGCC ACCCGCTGGT CACGGGGCTG CTGGACCAGT TTGAGACCCG
 801 CAAGACCCTC ATCCTCATCC TGGAGCTGTG CTCATCCGAG GAGCTGCTGG
 851 ACCGCCTGTA CAGGAAGGGC GTGGTGACGG AGGCCGAGGT CAAGGTCTAC
 901 ATCCAGCAGC TGGTGGAGGG GCTGCACTAC CTGCACAGCC ATGGCGTTCT
 951 CCACCTGGAC ATAAAGCCCT CTAACATCCT GATGGTGCAT CCTGCCCGGG
1001 AAGACATTAA AATCTGCGAC TTTGGCTTTG CCCAGAACAT CACCCCAGCA
1051 GAGCTGCAGT TCAGCCAGTA CGGCTCCCCT GAGTTCGTCT CCCCCGAGAT
1101 CATCCAGCAG AACCCTGTGA GCGAAGCCTC CGACATTTGG GCCATGGGTG
1151 TCATCTCCTA CCTCAGCCTG ACCTGCTCAT CCCCATTTGC CGGCGAGAGT
1201 GACCGTGCCA CCCTCCTGAA CGTCCTGGAG GGGCGCGTGT CATGGAGCAG
1251 CCCCATGGCT GCCCACCTCA GCGAAGACGC CAAAGACTTC ATCAAGGCTA
1301 CGCTGCAGAG AGCCCCTCAG GCCCGGCCTA GTGCGGCCCA GTGCCTCTCC
1351 CACCCCTGGT TCCTGAAATC CATGCCTGCG GAGGAGGCCC ACTTCATCAA
1401 CACCAAGCAG CTCAAGTTCC TCCTGGCCCG AAGTCGCTGG CAGCGTTCCC
1451 TGATGAGCTA CAAGTCCATC CTGGTGATGC GCTCCATCCC TGAGCTGCTG
1501 CGGGGCCCAC CCGACAGCCC CTCCCTCGGC GTAGCCCGGC ACCTCTGCAG
1551 GGACACTGGT GGCTCCTCCA GTTCCTCCTC CTCCTCTGAC AACGAGCTCG
1601 CCCCATTTGC CCGGGCTAAG TCACTGCCAC CCTCCCCGGT GACACACTCA
1651 CCACTGCTGC ACCCCCGGGG CTTCCTGCGG CCCTCGGCCA GCCTGCCTGA
1701 GGAAGCCGAG GCCAGTGAGC GCTCCACCGA GGCCCCAGCT CCGCCTGCAT
1751 CTCCCGAGGG TGCCGGGCCA CCGGCCGCCC AGGGCTGCGT GCCCCGGCAC
1801 AGCGTCATCC GCAGCCTGTT CTACCACCAG GCGGGTGAGA GCCCTGAGCA
1851 CGGGGCCCTG GCCCCGGGGA GCAGGCGGCA CCCGGCCCGG CGGCGGCACC
1901 TGCTGAAGGG CGGCTACATT GCGGGGCGC TGCCAGGCCT GCGCGAGCCA
1951 CTGATGGAGC ACCGCGTGCT GGAGGAGGAG GCCGCCAGGG AGGAGCAGGC
2001 CACCCTCCTG GCCAAAGCCC CCTCATTCGA GACTGCCCTC CGGCTGCCTG
2051 CCTCTGGCAC CCACTTGGCC CCTGGCCACA GCCACTCCCT GGAACATGAC
2101 TCTCCGAGCA CCCCCCGCCC CTCCTCGGAG GCCTGCGGTG AGGCACAGCG
2151 ACTGCCTTCA GCCCCCTCCC GGGGGGCCCC TATCAGGGAC ATGGGGCACC
2201 CTCAGGGCTC CAAGCAGCTT CCATCCACTG GTGGCCACCC AGGCACTGCT
2251 CAGCCAGAGA GGCCATCCCC GGACAGCCCT TGGGGCAGC CAGCCCCTTT
2301 CTGCCACCCC AAGCAGGGTT CTGCCCCCCA GGAGGGCTGC AGCCCCCACC
2351 CAGCAGTTGC CCCATGCCCT CCTGGCTCCT TCCCTCCAGG ATCTTGCAAA
2401 GAGGCCCCCT TAGTACCCTC AAGCCCCTTC TTGGGACAGC CCCAGGCACC
2451 CCCTGCCCCT GCCAAAGCAA GCCCCCCATT GGACTCTAAG ATGGGGCCTG
2501 GAGACATCTC TCTTCCTGGG AGGCCAAAAC CCGGCCCCTG CAGTTCCCCA
2551 GGGTCAGCCT CCCAGGCGAG CTCTTCCCAA GTGAGCTCCC TCAGGGTGGG
2601 CTCCTCCCAG GTGGGCACAG AGCCTGGCCC CTCCCTGGAT GCGGAGGGCT
2651 GGACCCAGGA GGCTGAGGAT CTGTCCGACT CCACACCCAC CTTGCAGCGG
2701 CCTCAGGAAC AGGTGACCAT GCGCAAGTTC TCCCTGGGTG GTCGCGGGGG
2751 CTACGCAGGC GTGGCTGGCT ATGGCACCTT TGCCTTTGGT GGAGATGCAG
2801 GGGGCATGCT GGGGCAGGGG CCCATGTGGG CAGGATAGC CTGGGCTGTG
2851 TCCCAGTCGG AGGAGGAGGA GCAGGAGGAG GCCAGGGCTG AGTCCCAGTC
2901 GGAGGAGCAG CAGGAGGCCA GGGCTGAGAG CCCACTGCCC CAGGTCAGTG
2951 CAAGGCCTGT GCCTGAGGTC GGCAGGGCTC CCACCAGGAG CTCTCCAGAG
3001 CCCACCCCAT GGAGGACAT CGGGCAGGTC TCCCTGGTGC AGATCCGGGA
3051 CCTGTCAGGT GATGCGGAGG CGGCCGACAC AATATCCCTG GACATTTCCG
3101 AGGTGGACCC CGCCTACCTC AACCTCTCAG ACCTGTACGA TATCAAGTAC
3151 CTCCCATTCG AGTTTATGAT CTTCAGGAAA GTCCCCAAGT CCGCTCAGCC
3201 AGAGCCGCCC TCCCCCATGG CTGAGGAGGA GCTGGCCGAG TTCCCGGAGC
3251 CCACGTGGCC CTGGCCAGGT GAACTGGGCC CCACGCAGG CCTGGAGATC
3301 ACAGAGGAGT CAGAGGATGT GGACGCGCTG CTGGCAGAGG CTGCCGTGGG
3351 CAGGAAGCGC AAGTGGTCCT CGCCGTCACG CAGCCTCTTC CACTTCCCTG
3401 GGAGGCACCT GCCGCTGGAT GAGCCTGCAG AGCTGGGGCT GCGTGAGAGA
3451 GTGAAGGCCT CCGTGGAGCA CATCTCCCGG ATCCTGAAGG GCAGGCCGGA
```

FIGURE 1A

```
3501  AGGTCTGGAG AAGGAGGGGC CCCCCAGGAA GAAGCCAGGC CTTGCTTCCT
3551  TCCGGCTCTC AGGTCTGAAG AGCTGGGACC GAGCGCCGAC ATTCCTAAGG
3601  GAGCTCTCAG ATGAGACTGT GGTCCTGGGC CAGTCAGTGA CACTGGCCTG
3651  CCAGGTGTCA GCCCAGCCAG CTGCCCAGGC CACCTGGAGC AAAGACGGAG
3701  CCCCCCTGGA GAGCAGCAGC CGTGTCCTCA TCTCTGCCAC CCTCAAGAAC
3751  TTCCAGCTTC TGACCATCCT GGTGGTGGTG GCTGAGGACC TGGGTGTGTA
3801  CACCTGCAGC GTGAGCAATG CGCTGGGGAC AGTGACCACC ACGGGCGTCC
3851  TCCGGAAGGC AGAGCGCCCC TCATCTTCGC CATGCCCGGA TATCGGGGAG
3901  GTGTACGCGG ATGGGGTGCT GCTGGTCTGG AAGCCCGTGG AATCCTACGG
3951  CCCTGTGACC TACATTGTGC AGTGCAGCCT AGAAGGCGGC AGCTGGACCA
4001  CACTGGCCTC CGACATCTTT GACTGCTGCT ACCTGACCAG CAAGCTCTCC
4051  CGGGGTGGCA CCTACACCTT CCGCACGGCA TGTGTCAGCA AGGCAGGAAT
4101  GGGTCCCTAC AGCAGCCCCT CGGAGCAAGT CCTCCTGGGA GGGCCCAGCC
4151  ACCTGGCCTC TGAGGAGGAG AGCCAGGGGC GGTCAGCCCA ACCCCTGCCC
4201  AGCACAAAGA CCTTCGCATT CCAGACACAG ATCCAGAGGG GCCGCTTCAG
4251  CGTGGTGCGG CAATGCTGGG AGAAGGCCAG CGGGCGGGCG CTGGCCGCCA
4301  AGATCATCCC CTACCACCCC AAGGACAAGA CAGCAGTGCT GCGCGAATAC
4351  GAGGCCCTCA AGGGCCTGCG CCACCCGCAC CTGGCCCAGC TGCACGCAGC
4401  CTACCTCAGC CCCCGGCACC TGGTGCTCAT CTTGGAGCTG TGCTCTGGGC
4451  CCGAGCTGCT CCCCTGCCTG GCCGAGAGGG CCTCCTACTC AGAATCTGAG
4501  GTGAAGGACT ACCTGTGGCA GATGTTGAGT GCCACCCAGT ACCTGCACAA
4551  CCAGCACATC CTGCACCTGG ACCTGAGGTC CGAGAACATG ATCATCACCG
4601  AATACAACCT GCTCAAGGTC GTGGACCTGG GCAATGCACA GAGCCTCAGC
4651  CAGGAGAAGG TGCTGCCCTC AGACAAGTTC AAGGACTACC TAGAGACCAT
4701  GGCTCCAGAG CTCCTGGAGG GCCAGGGGGC TGTTCCACAG ACAGACATCT
4751  GGGCCATCGG TGTGACAGCC TTCATCATGC TGAGCGCCGA GTACCCGGTG
4801  AGCAGCGAGG GTGCACGCGA CCTGCAGAGA GGACTGCGCA AGGGGCTGGT
4851  CCGGCTGAGC CGCTGCTACG CGGGGCTGTC CGGGGGCGCC GTGGCCTTCC
4901  TGCGCAGCAC TCTGTGCGCC CAGCCCTGGG GCCGGCCCTG CGCGTCCAGC
4951  TGCCTGCAGT GCCCGTGGCT AACAGAGGAG GGCCCGGCCT GTTCGCGGCC
5001  CGCGCCCGTG ACCTTCCCTA CCGCGCGGCT GCGCGTCTTC GTGCGCAATC
5051  GCGAGAAGAG ACGCGCGCTG CTGTACAAGA GGCACAACCT GGCCCAGGTG
5101  CGCTGAGGGT CGCCCCGGCC ACACCCTTGG TCTCCCCGCT GGGGGTCGCT
5151  GCAGACGCGC CAATAAAAAC GCACAGCCGG GCGAGAAAAA AAAAAAAAA
5201  AAAAAAA  (SEQ ID NO:1)
```
FEATURES:
Start: 109
Stop: 5104
Homologous proteins:
Top BLAST Hits:

|  | Score | E |
|---|---|---|
| gi|7242949|dbj|BAA92535.1| (AB037718) KIAA1297 protein [Homo sa... | 425 | e-117 |
| gi|8928460|sp|O75962|TRIO_HUMAN TRIPLE FUNCTIONAL DOMAIN PROTEI... | 229 | 1e-58 |
| gi|6005922|ref|NP_009049.1| triple functional domain (PTPRF int... | 229 | 1e-58 |
| gi|3024081|sp|Q15746|KMLS_HUMAN MYOSIN LIGHT CHAIN KINASE, SMOO... | 206 | 2e-51 |
| gi|90103|pir||A41674 myosin-light-chain kinase (EC 2.7.1.117), ... | 205 | 4e-51 |
| gi|7239696|gb|AAC18423.2| (U48959) myosin light chain kinase [H... | 204 | 6e-51 |
| gi|7239698|gb|AAD15921.2| (AF069601) myosin light chain kinase ... | 204 | 6e-51 |
| gi|1103677|emb|CAA62378.1| (X90870) myosin-light-chain kinase [... | 204 | 6e-51 |
| gi|3024085|sp|Q28824|KMLS_BOVIN MYOSIN LIGHT CHAIN KINASE, SMOO... | 203 | 1e-50 |
| gi|2851405|sp|P29294|KMLS_RABIT MYOSIN LIGHT CHAIN KINASE, SMOO... | 203 | 1e-50 |
| gi|3982821|gb|AAC83683.1| (AF081663) myosin light chain kinase ... | 198 | 3e-49 |
| gi|3982823|gb|AAC83684.1| (AF081664) myosin light chain kinase ... | 198 | 3e-49 |
| gi|3982827|gb|AAC83686.1| (AF081666) myosin light chain kinase ... | 198 | 3e-49 |
| gi|3982807|gb|AAC83676.1| (AF081656) myosin light chain kinase ... | 198 | 3e-49 |

BLAST dbEST hit:
gi|7958129 /dataset=dbest /taxon=960...                                    1283    0.0
EXPRESSION INFORMATION FOR MODULATORY USE:
From BLAST dbEST hit:
gi|7958129  Human Colon carcinoma
From PCR-based tissue screening panels:
Human Placenta
Human Kidney
Human Lung
Human skeletal muscle
Human heart
Human fetal whole brain

FIGURE 1B

```
   1 MGCCRLGCGG CSVAHSVSQG LTNHPSMVGC GWHPGLCGWG GGLHSSLPAL
  51 PGPPSMQVTI EDVQAQTGGT AQFEAIIEGD PQPSVTWYKD SVQLVDSTRL
 101 SQQQEGTTYS LVLRHVASKD AGVYTCLAQN TGGQVLCKAE LLVLGGDNEP
 151 DSEKQSHRRK LHSFYEVKEE IGRGVFGFVK RVQHKGNKIL CAAKFIPLRS
 201 RTRAQAYRER DILAALSHPL VTGLLDQFET RKTLILILEL CSSEELLDRL
 251 YRKGVVTEAE VKVYIQQLVE GLHYLHSHGV LHLDIKPSNI LMVHPAREDI
 301 KICDFGFAQN ITPAELQFSQ YGSPEFVSPE IIQQNPVSEA SDIWAMGVIS
 351 YLSLTCSSPF AGESDRATLL NVLEGRVSWS SPMAAHLSED AKDFIKATLQ
 401 RAPQARPSAA QCLSHPWFLK SMPAEEAHFI NTKQLKFLLA RSRWQRSLMS
 451 YKSILVMRSI PELLRGPPDS PSLGVARHLC RDTGGSSSSS SSSDNELAPF
 501 ARAKSLPPSP VTHSPLLHPR GFLRPSASLP EEAEASERST EAPAPPASPE
 551 GAGPPAAQGC VPRHSVIRSL FYHQAGESPE HGALAPGSRR HPARRRHLLK
 601 GGYIAGALPG LREPLMEHRV LEEEAAREEQ ATLLAKAPSF ETALRLPASG
 651 THLAPGHSHS LEHDSPSTPR PSSEACGEAQ RLPSAPSGGA PIRDMGHPQG
 701 SKQLPSTGGH PGTAQPERPS PDSPWGQPAP FCHPKQGSAP QEGCSPHPAV
 751 APCPPGSFPP GSCKEAPLVP SSPFLGQPQA PPAPAKASPP LDSKMGPGDI
 801 SLPGRPKPGP CSSPGSASQA SSSQVSSLRV GSSQVGTEPG PSLDAEGWTQ
 851 EAEDLSDSTP TLQRPQEQVT MRKFSLGGRG GYAGVAGYGT FAFGGDAGGM
 901 LGQGPMWARI AWAVSQSEEE EQEEARAESQ SEEQQEARAE SPLPQVSARP
 951 VPEVGRAPTR SSPEPTPWED IGQVSLVQIR DLSGDAEAAD TISLDISEVD
1001 PAYLNLSDLY DIKYLPFEFM IFRKVPKSAQ PEPPSPMAEE ELAEFPEPTW
1051 PWPGELGPHA GLEITEESED VDALLAEAAV GRKRKWSSPS RSLFHFPGRH
1101 LPLDEPAELG LRERVKASVE HISRILKGRP EGLEKEGPPR KKPGLASFRL
1151 SGLKSWDRAP TFLRELSDET VVLGQSVTLA CQVSAQPAAQ ATWSKDGAPL
1201 ESSSRVLISA TLKNFQLLTI LVVVAEDLGV YTCSVSNALG TVTTTGVLRK
1251 AERPSSSPCP DIGEVYADGV LLVWKPVESY GPVTYIVQCS LEGGSWTTLA
1301 SDIFDCCYLT SKLSRGGTYT FRTACVSKAG MGPYSSPSEQ VLLGGPSHLA
1351 SEEESQGRSA QPLPSTKTFA FQTQIQRGRF SVVRQCWEKA SGRALAAKII
1401 PYHPKDKTAV LREYEALKGL RHPHLAQLHA AYLSPRHLVL ILELCSGPEL
1451 LPCLAERASY SESEVKDYLW QMLSATQYLH NQHILHLDLR SENMIITEYN
1501 LLKVVDLGNA QSLSQEKVLP SDKFKDYLET MAPELLEGQG AVPQTDIWAI
1551 GVTAFIMLSA EYPVSSEGAR DLQRGLRKGL VRLSRCYAGL SGGAVAFLRS
1601 TLCAQPWGRP CASSCLQCPW LTEEGPACSR PAPVTFPTAR LRVFVRNREK
1651 RRALLYKRHN LAQVR (SEQ ID NO:2)
```

FEATURES:
Functional domains and key regions:
Prosite results:

[1] PDOC00001 PS00001 ASN_GLYCOSYLATION
N-glycosylation site 1005-1008 NLSD

---

[2] PDOC00004 PS00004 CAMP_PHOSPHO_SITE
cAMP- and cGMP-dependent protein kinase phosphorylation site Number of matches: 2
    1     872-875 RKFS
    2  1084-1087 RKWS

---

[3] PDOC00005 PS00005 PKC_PHOSPHO_SITE
Protein kinase C phosphorylation site Number of matches: 23
    1    97-99  STR
    2   152-154  SEK
    3   156-158  SHR
    4   230-232  TRK
    5   364-366  SDR
    6   450-452  SYK
    7   536-538  SER
    8   588-590  SRR
    9   668-670  TPR
   10   762-764  SCK
   11   827-829  SLR
   12   870-872  TMR
   13   947-949  SAR
   14  1147-1149  SFR

FIGURE 2A

```
    15  1203-1205  SSR
    16  1211-1213  TLK
    17  1310-1312  TSK
    18  1320-1322  TFR
    19  1365-1367  STK
    20  1391-1393  SGR
    21  1434-1436  SPR
    22  1521-1523  SDK
    23  1638-1640  TAR
```

[4] PDOC00006 PS00006 CK2_PHOSPHO_SITE
Casein kinase II phosphorylation site

```
Number of matches: 21
     1      59-62   TIED
     2     163-166  SFYE
     3     242-245  SSEE
     4     257-260  TEAE
     5     312-315  TPAE
     6     459-462  SIPE
     7     491-494  SSSD
     8     493-496  SDNE
     9     528-531  SLPE
    10     762-765  SCKE
    11     915-918  SQSE
    12     929-932  SQSE
    13     917-920  SEEE
    14    1351-1354 SEEE
    15     915-918  SQSE
    16     929-932  SQSE
    17     961-964  SSPE
    18     966-969  TPWE
    19     997-1000 SEVD
    20    1336-1339 SPSE
    21     917-920  SEEE
```

[5] PDOC00008 PS00008 MYRISTYL
N-myristoylation site

```
Number of matches: 27
     1       7-12   GCGGCS
     2      10-15   GCSVAH
     3      41-46   GGLHSS
     4      42-47   GLHSSL
     5     106-111  GTTYSL
     6     122-127  GVYTCL
     7     133-138  GQVLCK
     8     484-489  GGSSSS
     9     485-490  GSSSSS
    10     601-606  GGYIAG
    11     606-611  GALPGL
    12     708-713  GGHPGT
    13     877-882  GGRGGY
    14     880-885  GGYAGV
    15     894-899  GGDAGG
    16     898-903  GGMLGQ
    17    1061-1066 GLEITE
    18    1174-1179 GQSVTL
    19    1229-1234 GVYTCS
    20    1240-1245 GTVTTT
    21    1293-1298 GGSWTT
    22    1294-1299 GSWTTL
    23    1316-1321 GGTYTF
    24    1508-1513 GNAQSL
    25    1575-1580 GLRKGL
    26    1589-1594 GLSGGA
    27    1592-1597 GGAVAF
```

FIGURE 2B

[6] PDOC00009 PS00009 AMIDATION
Amidation site 1080-1083 VGRK

[7] PDOC00373 PS00343 GRAM_POS_ANCHORING
Gram-positive cocci surface proteins 'anchoring' hexapeptide 704-709 LPSTGG

[8] PDOC00100 PS00107 PROTEIN_KINASE_ATP
Protein kinases ATP-binding region signature 171-194 IGRGVFGFVKRVQHKGNKILCAAK

[9] PDOC00100 PS00108 PROTEIN_KINASE_ST
Serine/Threonine protein kinases active-site signature 280-292 VLHLDIKPSNILM

[10] PDOC00100 PS00109 PROTEIN_KINASE_TYR
Tyrosine protein kinases specific active-site signature 1484-1496 ILHLDLRSENMII

[11] PDOC00565 PS00659 GLYCOSYL_HYDROL_F5
Glycosyl hydrolases family 5 signature 142-151 LVLGGDNEPD

BLAST Alignment to Top Hits:
>gi|7242949|dbj|BAA92535.1| (AB037718) KIAA1297 protein [Homo sapiens]
            Length = 2242

Score =  425 bits (1081), Expect = e-117
 Identities = 305/876 (34%), Positives = 423/876 (47%), Gaps = 106/876 (12%)

```
Query:  54  PSMQVTIEDVQAQTGGTAQFEAIIEGDPQPSVTWYKDSVQLVDSTRLSQQQEGTTYSLVL 113
            P   + +EDV+    G TA+F ++EG P P + WYKD V L +S+ +S    E    SLV+
Sbjct: 504  PRFESIMEDVEVGAGETARFAVVVEGKPLPDIMWYKDEVLLTESSHVSFVYEENECSLVV 563

Query: 114  RHVASKDAGVYTCLAQNTGGQVLCKAELLVLGGDN----EPDSEKQSHR-RKLHSFYEVK 168
            ++D  GVYTC AQN  G+V CKAEL V       E    E + HR R+L   FY++
Sbjct: 564  LSTGAQDGGVYTCTAQNLAGEVSCKAELAVHSAQTAMEVEGVGEDEDHRGRRLSDFYDIH 623

Query: 169  EEIGRGVFGFVKRVQHKGNKILCAAKFIPLRSRTRAQAYRERDILAALSHPLVTGLLDQF 228
            +EIGRG F +++R+ + +    AAKFIP +++ +A A RE +LA L H  V    + F
Sbjct: 624  QEIGRGAFSYLRRIVERSSGLEFAAKFIPSQAKPKASARREARLLARLQHDCVLYFHEAF 683

Query: 229  ETRKTLILILELCSSEELLDRLYRKGVVTEAEVKVYIQQLVEGLHYLHSHGVLHLDIKPS 288
            E R+ L+++ ELC+ EELL+R+ RK  V E+E++ Y++Q++EG+HYLH    VLHLD+KP
Sbjct: 684  ERRGLVIVTELCT-EELLERIARKPTVCESEIRAYMRQVLEGIHYLHQSHVLHLDVKPE 742

Query: 289  NILMVHPA--REDIKICDFGFAQNITPAELQFSQYGSPEFVSPEIIQQNPVSEASDIWAM 346
            N+L+  A   + ++ICDFG AQ +TP E Q+ QYG+PEFV+PEI+ Q+PVS  +DIW +
Sbjct: 743  NLLVWDGAAGEQQVRICDFGNAQELTPGEPQYCQYGTPEFVAPEIVNQSPVSGVTDIWPV 802

Query: 347  GVISYLSLTCSSPFAGESDRATLLNVLEGRVSWSSPMAAHLSEDAKDF-IKATLQRAPQA 405
            GV+++++L LT  SPF GE+DR TL+N+      V++        LS +A+ F IK  +Q   +
Sbjct: 803  GVVAFLCLTGISPFVGENDRTTLMNIRNYNVAFEETTFLSLSREARGFLIKVLVQ--DRL 860

Query: 406  RPSAAQCLSHPWFLKSMPAEEAHFINTKQLKFLLARSRWQRSLMSYKSILVMRSIPELLR 465
            RP+A + L HPWF       E   ++T LK L+R RWQRS +SYK  LV+R IPELLR
Sbjct: 861  RPTAEETLEHPWFKTQAKGAE---VSTDHLKLFLSRRRWQRSQISYKCHLVLRPIPELLR 917

Query: 466  GPPDSPSLGVARHLCRDTGGSSSSSSSSDNELAPFARAK-----------SLPPSPVTH 513
            PP+   + R   +GG SSSS S + EL                        SL   P
Sbjct: 918  APPERVWVTMPRR-PPPSGGLSSSSDSEEEELEELPSVPRPLQPEFSGSRVSLTDIPTED 976

Query: 514  SPLLHPRGFLRPSASLPEEAEASERSTEAPAPPASPEGAGPPAAQGCVPRHSVI------ 567
```

FIGURE 2C

```
                 L   P           E+   A  +   EAP+P A P      PAA  G   PR    +
Sbjct:  977  EALGTPETGAATPMDWQEQGRAPSQDQEAPSPEALPSPGQEPAA-GASPRRGELRRGSSA  1035

Query:  568  ------------RSLFYHQAGESPEHGALAPG--------------SRRHPARRRHLLK   600
                          R L   + E P+  +  PG              ++R A R+ LL+
Sbjct: 1036  ESALPRAGPRELGRGLHKAASVELPQRRSPGPGATRLARGGLGEGEYAQRLQALRQRLLR  1095

Query:  601  GGYIAGALPGLREPLMEH----------RVLEEEAAREEQATL----LAKAPSFETALR   645
             GG   G + GLR PL+E            R   EAA  Q L    L K+ SF
Sbjct: 1096  GGPEDGKVSGLRGPLLESLGGRARDPRMARAASSEAAPHHQPPLENRGLQKSSSFSQGEA  1155

Query:  646  LPASGTHLAPGHSHSLEHDSPSTPR----PSSEACGEAQRLPSAPSGGAPIRDMGHPQGS   701
                P  G H  G  +      R        PS A EAQ  PS+P+          P
Sbjct: 1156  EP-RGRHRRAGAPLEIPVARLGARRLQESPSLSALSEAQ--PSSPA---------RPSAP  1203

Query:  702  KQLPSTGGHPGTAQPERPSPDSPWGQPAPFCHPKQGSAPQEGCSPHPAVAPCPP----GS   757
             K  PST    P +A+P  +P      PAP    PQ   AP+     P A  PP    +
Sbjct: 1204  K--PST---PKSAEPSATTPSDAPQPPAP--QPAQDKAPEPRPEPVRASKPAPPPQALQT  1256

Query:  758  FPPGSCKEAPLVPSSPFLGQPQAPPAPAKASPPLDSKMGPGDISLPGRPKPGPCSSPGSA   817
                    A ++ S    G Q P+   A+PP +  K          + P  PG     +
Sbjct: 1257  LALPLTPYAQIIQSLQLSGHAQG-PSQGPAAPPSEPKPHAAVFARVASPPPG--APEKRV  1313

Query:  818  SQASSSQVSSLRVGSSQVGTEPGPSLDAEGWTQEAE   853
              A   V +        +   V  PG SL  +    E+E
Sbjct: 1314  PSAGGPPVLAEKARVPTVPPRPGSSLSSSIENLESE  1349    (SEQ ID NO:4)

Score =  210 bits (529), Expect = 1e-52
 Identities = 111/281 (39%), Positives = 156/281 (55%), Gaps = 2/281 (0%)

Query: 1336  SPSEQVLLGGPSHLASEEESQGRSAQPLPSTKTFAFQTQIQRGRFSVVRQCWEKASGRAL  1395
             SP+++V+    S     S     +G  + +  P   K F + + RGRF VVR C E A+GR
Sbjct: 1952  SPAKEVVSSPGSSPRSSPRPEGTTLRQGPPQKPYTFLEEKARGRFGVVRACRENATGRTF  2011

Query: 1396  AAKIIPYHPKDKTAVLREYEALKGLRHPHLAQLHAAYLSPRHLVLILELCSGPELLPCLA  1455
             AAKI+PY   + K  VL+EYE L+  L H  + LH AY++PR+LVLI E C   ELL  L+
Sbjct: 2012  VAKIVPYAAEGKPRVLQEYEVLRTLHHERIMSLHEAYITPRYLVLIAESCGNRELLCGLS  2071

Query: 1456  ERASYSESEVKDYLWQMLSATQYLHNQILHLDLRSENMIITEYNLLKVVDLGNAQSLSQ   1515
             +R  YSE +V  Y+ Q+L    YLH  H+LHLD++  +N+++   N LK+VD G+AQ   +
Sbjct: 2072  DRFRYSEDDVATYMVQLLQGLDYLHGHHVLHLDIKPDNLLLAPDNALKIVDFGSAQPYNP  2131

Query: 1516  EKVLPSDKFKDYLETMAPELLEGQGAVPQTDIWAIGVTAFIMLSAEYPVSSEGARDLQRG  1575
              + + P       LE MAPE+++G+      TDIW GV +IMLS    P    ++ +
Sbjct: 2132  QALRPLGHRTGTLEFMAPEMVKGEPIGSATDIWGAGVLTYIMLSGRSPFYEPDPQETEAR  2191

Query: 1576  LRKGLVRLSRCYAGLSGGAVAFLRSTLCAQPWGRPCASSCL  1616
              + G    + Y  S  A   FLR  L   PW RP  SSCL
Sbjct: 2192  IVGGRFDAFQLYPNTSQSATLFLRKVLSVHPWSRP--SSCL  2230    (SEQ ID NO:5)

Score =  170 bits (426), Expect = 1e-40
 Identities = 168/574 (29%), Positives = 256/574 (44%), Gaps = 42/574 (7%)

Query: 1103  LDEP--AELGLRERVKASVEHISRILKGRPEGLEKEGPPRKKPGLASFRLSGLKSWDRAP  1160
             L EP    A  GLR+         V+HI R+L     +    K PP +    L    + + AP
Sbjct:  358  LREPGWAATGLRK----GVQHIFRVLSTTVKSSSKPSPPSEPVQL----LEHGPTLEEAP   409

Query: 1161  TFLRELSDETVVLGQSVTLACQVSAQPAAQATW-SKDGAPLESSSRVL-ISATLKNFQLL  1218
                L +        VV GQ ++         + AQ   W S GA LE+ +   V +S       L
Sbjct:  410  AMLDKPDIVYVVEGQPASVTVTFN-HVEAQVVWRSCRGALLEARAGVYELSQPDDDQYCL   468

Query: 1219  TILVVVAEDLGVYTCSVSNALGTVTTTGVLRKAERPS-SSPCPDI----GEVYADGVLLV  1273
              I    V   D+G  TC+   N  GT T T  +  L  AE P     S   D+   GE     V++
Sbjct:  469  RICRVSRRDMGALTCTARNRHGTQTCSVTELAEAPRFESIMEDVEVGAGETARFAVVVE   528

Query: 1274  WKPVESYGPVTYIVQCSLEGGSWTTLASDIFDCCY--LTSKLSRGGTYTFRTACVSKAGM  1331
              KP+       Y +    L S          + +C   L++     GG YT    C  ++
Sbjct:  529  GKPLPDI--MWYKDEVLLTESSHVSFVYEENECSLVVLSTGAQDGGVYT----CTAQNLA   582
```

FIGURE 2D

```
Query:  1332  GPYSSPSEQVLLGGPSHLASEEESQGRSAQPLPSTKTFAFQTQIQRGRFSVVRQCWEKAS  1391
              G  S  +E  +     + +  E    +    +       +I RG FS +R+  E++S
Sbjct:   583  GEVSCKAELAVHSAQTAMEVGVGEDEDHRGRRLSDFYDIHQEIGRGAFSYLRRIVERSS   642

Query:  1392  GRALAAKIIPYHPKDKTAVLREYEALKGLRHPHLAQLHAAYLSPRHLVLILELCSGPELL  1451
              G   AAK IP   K K  +  RE   L  L+H  +    H A+   R LV++ ELC+  ELL
Sbjct:   643  GLEFAAKFIPSQAKPKASARREARLLARLQHDCVLYFHEAFERRRGLVIVTELCT-EELL  701

Query:  1452  PCLAERASYSESEVKDYLWQMLSATQYLHNQHILHLDLRSENMIITE----YNLLKVVDL  1507
              +A  +  +    ESE++ Y+ Q+L    YLH   H+LHLD++  EN+++  +         +++ D
Sbjct:   702  ERIARKPTVCESEIRAYMRQVLEGIHYLHQSHVLHLDVKPENLLVWDGAAGEQQVRICDF   761

Query:  1508  GNAQSLSQEKVLPSDKFKDYLETMAPELLEGQGAVPQTDIWAIGVTAFIMLSAEYPVSSE  1567
              GNAQ L+  +     P        E +APE++        TDIW  +GV AF+  L+     P     E
Sbjct:   762  GNAQELTPGE--PQYCQYGTPEFVAPEIVNQSPVSGVTDIWPVGVVAFLCLTGISPFVGE   819

Query:  1568  GARDLQRGLRKGLVRLSR-CYAGLSGGAVAFLRSTLCAQPWGRPCASSCLQCPWLTEEGP  1626
                 R    +R    V         + LS A    FL    L Q   RP A    L+   PW    +
Sbjct:   820  NDRTTLMNIRNYNVAFEETTFLSLSREARGFLIKVL-VQDRLRPTAEETLEHPWFKTQ--  876

Query:  1627  ACSRPAPVTFPTARLRVFV-RNREKRRALLYKRH  1659
              ++  A V+   T  L++F+  R R  +R   + YK H
Sbjct:   877  --AKGAEVS--TDHLKLFLSRRRWQRSQISYKCH   906   (SEQ ID NO:6)

Score =  145 bits (362), Expect = 4e-33
Identities = 85/253 (33%), Positives = 135/253 (52%), Gaps = 5/253 (1%)

Query:   165  YEVKEEIGRGVFGFVKRVQHKGNKILCAAKFIPLRSRTRAQAYRERDILAALSHPLVTGL   224
              Y   EE RG FG V+ +              AK +P  +   + +   +E ++L   L H  +    L
Sbjct:  1985  YTFLEEKARGRFGVVRACRENATGRTFVAKIVPYAAEGKPRVLQEYEVLRTLHHERIMSL  2044

Query:   225  LDQFETRKTLILILELCSSEELLDRLYRKGVVTEAEVKVYIQQLVEGLHYLHSHGVLHLD   284
              + +  T + L+LI E C + ELL     L  +          +E +V   Y+  QL++GL YLH H  VLHLD
Sbjct:  2045  HEAYITPRYLVLIAESCGNRELLCGLSDRFRYSEDDVATYMVQLLQGLDYLHGHHVLHLD  2104

Query:   285  IKPSNILMVHPAREDIKICDFGFAQNITPAELQ--FSQYGSPEFVSPEIIQQNPVSEASD   342
              IKP N+L+        +KI DFG AQ     P  L+       + G+  EF++PE+++      P+   A+D
Sbjct:  2105  IKPDNLLLA--PDNALKIVDFGSAQPYNPQALRPLGHRTGTLEFMAPEMVKGEPIGSATD  2162

Query:   343  IWAMGVISYLSLTCSSPFAGESDRATLLNVLEGRVSWSSPMAAHLSEDAKDFIKATLQRA   402
              IW  GV++Y+ L+  SPF      +  T   ++ GR   +      + S+ A  F++     L
Sbjct:  2163  IWGAGVLTYIMLSGRSPFYEPDPQETEARIVGGRFD-AFQLYPNTSQSATLFLRKVLSVH  2221

Query:   403  PQARPSAAQCLSH   415
              P +RPS+  + H
Sbjct:  2222  PWSRPSSCLSVCH  2234   (SEQ ID NO:7)

Score =  128 bits (319), Expect = 4e-28
Identities = 81/245 (33%), Positives = 120/245 (48%), Gaps = 19/245 (7%)

Query:  1139  PRKKPGLASFRLSGL----------KSWDRAPTFLRELSDETVVLGQSVTLACQVSAQP  1187
              PRK  GL+   LS              D  P F +L D+ ++ G++  TL C   +A P
Sbjct:  1571  PRKDKGLSPPNLSASVQEELGHQYVRSESDFPPVFHIKLKDQVLLEGEAATLLCLPAACP  1630

Query:  1188  AAQATWSKDGAPLESSSRVLISATLKNFQLLTILVVVAEDLGVYTCSVSNALGTVTTTGV  1247
              A    +W KD    L S    V+I +       QLL+I        G+Y CS +N LG++T++
Sbjct:  1631  APHISWMKDKKSLRSEPSVIIVSCKDGRQLLSIPRAGKRHAGLYECSATNVLGSITSSCT  1690

Query:  1248  LRKAERPSSSPCPDIGEVYADGVLLVWKPVESYGPVTYIVQCSLEGGS-WTTLASDIFDC  1306
              +   A   P     P++  +  Y D  L++WKP +S  P TY ++    ++G S W    ++S  I DC
Sbjct:  1691  VAVARVPGKLAPPEVTQTYQDTALVLWKPGDSRAPCTYTLERRVDGESVWHPVSSGIPDC  1750

Query:  1307  CYLTSKLSRGGTYTFRTACVSKAGMGPYSSPSEQVLLGG-------PSHLASEEESQGRS  1359
              Y  + L G T  FR AC ++AG GP+S+ SE+V   +  G                PS    E               R
Sbjct:  1751  YYNVTHLPVGVTVRFRVACANRAGQGPFSNSSEKVFVRGTQDSSAVPSAAHQEAPVTSRP  1810

Query:  1360  AQPLP  1364
```

FIGURE 2E

```
                A+  P
Sbjct: 1811 ARARP 1815 (SEQ ID NO:8)

Score = 71.0 bits (171), Expect = 9e-11
 Identities = 41/115 (35%), Positives = 57/115 (48%), Gaps = 4/115 (3%)

Query:   60 IEDVQAQTGGTAQFEAIIEGDPQPSVTWYKDSVQLVDSTRLSQQQEGTTYSLVLRHVASK 119
            +EDV+   G  A+F+   I G P P VTW     + +S L +Q+G +SL + HV S+
Sbjct:   89 LEDVEVLEGRAARFDCKISGTPPPVVTWTHFGCPMEESENLRLRQDGGLHSLHIAHVGSE 148

Query:  120 DAGVYTCLAQNTGGQVLCKAELLVLGGDNEPDSEKQSHRRKLHSFYEVKEEIGRG 174
            D G+Y   A NT GQ  C A+L V    EP +    KL    + EE +G
Sbjct:  149 DEGLYAVSAVNTHGQAHCSAQLYV----EEPRTAASGPSSKLEKMPSIPEEPEQG 199   (SEQ ID NO:9)

Score = 60.1 bits (143), Expect = 2e-07
 Identities = 54/199 (27%), Positives = 81/199 (40%), Gaps = 12/199 (6%)

Query: 1160 PTFLRELSDETVVLGQSVTLACQVSAQPAAQATWSKDGAPLESSSRVLISATLKNFQLLT 1219
            P FLR L D  V L +   L CQV+  P   +W +G ++SS   ++   ++      L
Sbjct:  207 PDFLRPLQDLEVGLAKEAMLECQVTQLPYPTISWFHNGHRIQSSDDRRMT-QYRDVHRLV 265

Query: 1220 ILVVVAEDLGVYTCSVSNALGTVTTTGVLRKAERPSSSP--CPDIGEVYADGVLLVWKPV 1277
             +     + GVY  ++N LG    L +      P    P +    V    VL W P
Sbjct:  266 FPAVGPQHAGVYKSVIANKLGKAACYAHLYVTDVVPGPPDGAPQVVAVTGRMVTLTWNPP 325

Query: 1278 ESY------GPVTYIVQCSLEGG-SWTTLASDIFDCCYLTSKLSRGGTYTFRTACVSKAG 1330
             S        +TY VQ  + G   WT L + +   +  +L +G  + FR       +
Sbjct:  326 RSLDMAIDPDSLTYTVQHQVLGSDQWTALVTGLREPGWAATGLRKGVQHIFRVLSTTVKS 385

Query: 1331 MGPYSSPSE--QVLLGGPS 1347
              S PSE  Q+L  GP+
Sbjct:  386 SSKPSPPSEPVQLLEHGPT 404   (SEQ ID NO:10)

Score = 45.7 bits (106), Expect = 0.004
 Identities = 30/102 (29%), Positives = 45/102 (43%), Gaps = 1/102 (0%)

Query: 1159 APTFLRELSDETVVLGQSVTLACQVSAQPAAQATWSKDGAPLESSSRVLISATLKNFQLL 1218
            AP  F R L D  V+ G++     C++S  P        TW+  G P+E S  +       L
Sbjct:   82 APLFTRLLEDVEVLEGRAARFDCKISGTPPPVVTWTHFGCPMEESENLRLRQD-GGLHSL 140

Query: 1219 TILVVVAEDLGVYTCSVSNALGTVTTTGVLRKAERPSSSPCP 1260
              I V +ED G+Y   S N G    + L  E +++     P
Sbjct:  141 HIAHVGSEDEGLYAVSAVNTHGQAHCSAQLYVEEPRTAASGP 182   (SEQ ID NO:11)

Score = 43.8 bits (101), Expect = 0.015
 Identities = 58/217 (26%), Positives = 84/217 (37%), Gaps = 23/217 (10%)

Query:  619 RVLEEEAAREEQATLLAKAPSFETALRLPASGTHLAPGHSHSLEHDSPSTPRPSSEACGE 678
            R  ++ +A   A   S     R P S  LAP  +          T  PSS
Sbjct: 1788 RGTQDSSAVPSAAHQEAPVTSRPARARPPDSPTSLAPPLAPAAPTPPSVTVSPSSPPTPP 1847

Query:  679 AQRLPSAPSGGAPIRDMGHPQGSKQLPSTGGHPGTAPERPSPDSPWGQPAPFCHPKQGS 738
            +Q L S + G P+   + +       A+P  PS      +P PF
Sbjct: 1848 SQALSSLKAVGPPPQTP--PRRHRGLQAAR----PAEPTLPSTHVTPSEPKPFVLD---- 1897

Query:  739 APQEGCSPHPAVAPCPPGSFPPGSCKEAPLVPSSPFLGQPQAPPAPAKASPPLDSKMGPG 798
                + P  A  P  G  P S    P+  + F+  P AP  PA   PP +K+
Sbjct: 1898 ------TGTPIPASTPQGVKPVSS--STPVYVVTSFVSAPPAPEPPAPEPPPEPTKVTVQ 1949

Query:  799 DISLPGRPKPGPCSSPGSASQAS-SSQVSSLRVGSSQ 834
            +S   P       SSPGS+ ++S + ++LR G  Q
Sbjct: 1950 SLS----PAKEVVSSPGSSPRSSPRPEGTTLRQGPPQ 1982   (SEQ ID NO:12)

Score = 43.0 bits (99), Expect = 0.026
 Identities = 25/92 (27%), Positives = 44/92 (47%), Gaps = 4/92 (4%)
```

FIGURE 2F

```
Query:   54 PSMQVTIEDVQAQTGGTAQFEAIIEGDPQPSVTWYKDS--VQLVDSTRLSQQQEGTTYSL 111
            P   ++D++     A E  + G P P+++W+ +   +Q D R++Q ++    + L
Sbjct:  207 PDFLRPLQDLEVGLAKEAMLECQVTGLPYPTISWFHNGHRIQSSDDRRMTQYRD--VHRL 264

Query:  112 VLRHVASKDAGVYTCLAQNTGGQVLCKAELLV 143
            V   V   + AGVY  +  N G+   C A L V      (SEQ ID NO:13)
Sbjct:  265 VFPAVGPQHAGVYKSVIANKLGKAACYAHLYV 296
```

>gi|8928460|sp|O75962|TRIO_HUMAN TRIPLE FUNCTIONAL DOMAIN PROTEIN
        (PTPRF INTERACTING PROTEIN) >gi|3644048|gb|AAC43042.1|
        (AF091395) Trio isoform [Homo sapiens]
        Length = 3038

Score =  229 bits (579), Expect = 1e-58
 Identities = 143/418 (34%), Positives = 215/418 (51%), Gaps = 11/418 (2%)

```
Query:   53 PPSMQVTIEDVQAQTGGTAQFEAIIEGDPQPSVTWYKDSVQLVDST---RLSQQQEGTTY 109
            PP  + + +V +TG T     + G P+ S+TW       +++      +S    G
Sbjct: 2625 PPEFVIPLSEVTCETGETVVLRCRVCGRPKASITWKGPEHNTLNNDGHYSISYSDLGEA- 2683

Query:  110 SLVLRHVASKDAGVYTCLAQNTGGQVLCKAELLVLGGDNEPDSEKQSHRRKLHSFYEVKE 169
            +L + V ++D G+YTC+A N G    AL VLG     D   + +     SFY
Sbjct: 2684 TLKIVGVTTEDDGIYTCIAVNDMGSASSSASLRVLGPGM--DGIMVTWKDNFDSFYSEVA 2741

Query:  170 EIGRGVFGFVKRVQHKGNKILCAAKFIPLRSRTRAQAYRERDILAALSHPLVTGLLDQFE 229
            E+GRG F  VK+   KG K  A KF+ +   R Q  E IL +L HPL+ GLLD FE
Sbjct: 2742 ELGRGRFSVVKKCDQKGTKRAVATKFVNKKLMKRDQVTHELGILQSLQHPLLVGLLDTFE 2801

Query:  230 TRKTLILILELCSSEELLDRLYRKGVVTEAEVKVYIQQLVEGLHYLHSHGVLHLDIKPSN 289
            T   + IL+LE+    LLD + R G +TE +++  ++  +++E + YLH+    HLD+KP N
Sbjct: 2802 TPTSYILVLEMADQGRLLDCVVRWGSLTEGKIRAHLGEVLEAVRYLHNCRIAHLDLKPEN 2861

Query:  290 ILMVHP-AREDIKICDFGFAQNITPAELQFSQYGSPEFVSPEIIQQNPVSEASDIWAMGV 348
            IL+    A+   IK+ DFG A +            G+PEF +PEII  NPVS SD W++GV
Sbjct: 2862 ILVDESLAKPTIKLADFGDAVQLNTTYYIHQLLGNPEFAAPEIILGNPVSLTSDWSVGV 2921

Query:  349 ISYLSLTCSSPFAGESDRATLLNVLEGRVSWSSPMAAHLSEDAKDFIKATLQRAPQARPS 408
            ++Y+ L+  SPF  +S T  LN+     S+       +S+  AK+F+    LQ P  RPS
Sbjct: 2922 LTYVLLSGVSPFLDDSVEETCLNICRLDFSFPDDYFKGVSQKAKEFVCFLLQEDPAKRPS 2981

Query:  409 AAQCLSHPWFLKSMPAEEAHFINTKQLKFLLARSRWQ---RSLMSYKSILVMRSIPEL 463
            AA L   W L++           ++T +L    + R +Q   R + S K+ L R +P +
Sbjct: 2982 AALALQEQW-LQAGNGRSTGVLDTSRLTSFIERRKHQNDVRPIRSIKNFLQSRLLPRV 3038
(SEQ ID NO:14)
```

Score =  121 bits (300), Expect = 7e-26
 Identities = 82/280 (29%), Positives = 137/280 (48%), Gaps = 10/280 (3%)

```
Query: 1374 QIQRGRFSVVRQCWEKASGRALAAKIIPYHPKDKTAVLREYEALKGLRHPHLAQLHAAYL 1433
            ++ RGRFSV+++C +K + RA+A K +        + V E  L+ L+HP L L   +
Sbjct: 2742 ELGRGRFSVVKKCDQKGTKRAVATKFVNKKLMKRDQVTHELGILQSLQHPLLVGLLDTFE 2801

Query: 1434 SPRHLVLILELCSGPELLPCLAERASYSESEVKDYLWQMLSATQYLHNQHILHLDLRSEN 1493
            +P  + L+LE+   LL C+      S +E +++  L  ++LA +YLHN  I HLDL+ EN
Sbjct: 2802 TPTSYILVLEMADQGRLLDCVVRWGSLTEGKIRAHLGEVLEAVRYLHNCRIAHLDLKPEN 2861

Query: 1494 MIITE---YNLLKVVDLGNAQSLSQEKVLPSDKFKDYLETMAPELLEGQGAVPQTDIWAI 1550
            +++ E     +K+  D G+A  L+   +         E APE++ G      +D W++
Sbjct: 2862 ILVDESLAKPTIKLADFGDAVQLNTTYYI--HQLLGNPEFAAPEIILGNPVSLTSDTWSV 2919

Query: 1551 GVTAFIMLSAEYPVSSEGARDLQRGL-RKGLVRLSRCYAGLSGGAVAFLRSTLCAQPWGR 1609
            GV   +++LS  P +  +     + R    + G+S  A  F+   L   P R
Sbjct: 2920 GVLTYVLLSGVSPFLDDSVEETCLNICRLDFSFPDDYFKGVSQKAKEFVCFLLQEDPAKR 2979

Query: 1610 PCASSCLQCPWLTEEGPACSRPAPVTFPTARLRVFVRNRE 1649
            P A+  LQ  WL      A +  +    T+RL F+  R+
Sbjct: 2980 PSAALALQEQWL----QAGNGRSTGVLDTSRLTSFIERRK 3015  (SEQ ID NO:15)
```

FIGURE 2G

```
Score = 55.4 bits (131), Expect = 5e-06
Identities = 42/153 (27%), Positives = 70/153 (45%), Gaps = 17/153 (11%)

Query: 1128  GRPEGLEKEGPPRKKPGLASFRLSGLKS----WDRAPTFLRELSDETVVLGQSVTLACQV  1183
             G+ EG  + G  + + GL++      L +     +D  P F+ LS+ T   G++V L C+V
Sbjct: 2590  GKREGKLENGYRKSREGLSNKVSVKLLNPNYIYDVPPEFVIPLSEVTCETGETVVLRCRV  2649

Query: 1184  SAQPAAQATW-SKDGAPLESSSRVLISATLKNFQLLTILVVVAEDLGVYTCSVSNALGTV  1242
             +P A  TW    + L +    IS +      L I+ V  ED G+YTC    N +G+
Sbjct: 2650  CGRPKASITWKGPEHNTLNNDGHYSISYSDLGEATLKIVGVTTEDDGIYTCIAVNDMGSA  2709

Query: 1243  TTTGVLRKAERPSSSPCPDIGEVYADGVLLVWK  1275
             +++ LR            +   DG+++ WK
Sbjct: 2710  SSSASLR-----------VLGPGMDGIMVTWK  2730     (SEQ ID NO:16)

Score = 39.1 bits (89), Expect = 0.39
 Identities = 61/208 (29%), Positives = 76/208 (36%), Gaps = 65/208 (31%)

Query: 688   GGAPIRDMGHPQGSKQLPSTGGHPGTA--------QPERPSPD---------------S  723
             GGAP   GH G   S GG P T+        QP R P                S
Sbjct: 2252  GGAPSGGSGHSGGPS---SCGGAPSTSRSRPSRIPQPVRHHPPVLVSSAASSQAEADKMS  2308

Query: 724   PWGQPAPFCHPKQGSAPQEGCSPHPAVAPCPPGSFPPGSCKEAPLVSSPFLGQPQ----  779
                   P P   P  G+AP+  G  S    A  +  PPG+   GS +EA   +P     L  P+
Sbjct: 2309  GTSTPGPSL-PPPGAAPEAGPS---APSRRPPGADAEGSEREAEPIPKMKVLESPRKAA  2364

Query: 780   -----APPAPAK-----------------ASPPLDSKMGPGDISLPGRPKPGPCSSPGSA  817
                  +P APAK                 A+ PL+S +      SL   P P     P S
Sbjct: 2365  NASGSSPDAPAKDARASLGTLPLGKPRAGAASPLNSPLSSAVPSLGKEPFP-----PSSP  2419

Query: 818   SQASSSQVSSLRVG-SSQVG--TEPGPS  842
               Q   S SS+   +S+  G   T PG S
Sbjct: 2420  LQKGGSFWSSIPASPASRPGSFTFPGDS  2447     (SEQ ID NO:17)

>gi|3024081|sp|Q15746|KMLS_HUMAN MYOSIN LIGHT CHAIN KINASE, SMOOTH
             MUSCLE AND NON-MUSCLE ISOZYMES (MLCK) [CONTAINS: TELOKIN]
             Length = 1913

Score =  206 bits (518), Expect = 2e-51
 Identities = 104/298 (34%), Positives = 173/298 (57%), Gaps = 2/298 (0%)

Query: 159   RKLHSFYEVKEEIGRGVFGFVKRVQHKGNKILCAAKFIPLRSRTRAQAYRER-DILAALS  217
             +K+  FY+++E +G G FG V R+  K    + A KF     S    + R+   I+  L
Sbjct: 1458  QKVSDFYDIEERLGSGKFGQVFRLVEKKTRKVWAGKFFKAYSAKEKENIRQEISIMNCLH  1517

Query: 218   HPLVTGLLDQFETRKTLILILELCSSEELLDRLYRKGV-VTEAEVKVYIQQLVEGLHYLH  276
             HP +    +D FE +    ++++LE+ S  EL +R+     +TE E  Y++Q+ EG+ Y+H
Sbjct: 1518  HPKLVQCVDAFEEKANIVMLEIVSGGELFERIIDEDFELTERECIKYMRQISEGVEYIH  1577

Query: 277   SHGVLHLDIKPSNILMVHPAREDIKICDFGFAQNITPAELQFSQYGSPEFVSPEIIQQNP  336
                G++HLD+KP NI+ V+     IK+ DFG A+ +   A     +G+PEFV+PE+I   P
Sbjct: 1578  KQGIVHLDLKPENIMCVNKTGTRIKLIDFGLARRLENAGSLKVLFGTPEFVAPEVINYEP  1637

Query: 337   VSEASDIWAMGVISYLSLTCSSPFAGESDRATLLNVLEGRVSWSSPMAAHLSEDAKDFIK  396
             +S A+D+W++GVI Y+ ++    SPF G++D  TL NV       +    +S+DAKDFI
Sbjct: 1638  ISYATDMWSIGVICYILVSGLSPFMGDNDNETLANVTSATWDFDDEAFDEISDDAKDFIS  1697

Query: 397   ATLQRAPQARPSAAQCLSHPWFLKSMPAEEAHFINTKQLKFLLARSRWQRSLMSYKSI  454
              L++ +  R     QCL HPW +K      EA  ++  ++K  +AR +WQ++    + ++I
Sbjct: 1698  NLLKKDMKNRLDCTQCLQHPWLMKDTKNMEAKKLSKDRMKKYMARRKWQKTGNAVRAI  1755
 (SEQ ID NO:18)

Score =  127 bits (315), Expect = 1e-27
 Identities = 134/528 (25%), Positives = 219/528 (41%), Gaps = 55/528 (10%)

Query: 1132  GLEKEGPPRKKPGLASFRLSGLKSWDRAPTFLRELSDETVVLGQSVTLACQVSAQPAAQA  1191
              G E +   +KKP  +    +      P  ++   D+ V  G+SV L  +V+
Sbjct: 1215  GTESDATVKKKPAPKTPPKAAMP-----PQIIQFPEDQKVRAGESVELFGKVTGTQPITC  1269
```

FIGURE 2H

```
Query: 1192 TWSKDGAPLESSSRVLISATLKNFQLLTILVVVAEDLGVYTCSVSNALGT----VTTTGV 1247
             TW K    ++ S + +   +N    LTIL     E  GYT  V NLG+     V  T V
Sbjct: 1270 TWMKFRKQIQDSEHIKVENS-ENGSKLTILAARQEHCGCYTLLVENKLGSRQAQVNLT-V 1327

Query: 1248 LRKAERPSSSPCPDIGEVYADGVLLVWKPVESYGPVTYIVQCSLE-----GGSWTTLASD 1302
             + K + P+ +PC    ++ +  + L W    SY   + +  S+E         +W LA+
Sbjct: 1328 VDKPDPPAGTPCAS--DIRSSSLTLSWYG-SSYDGGSAVQSYSIEIWDSANKTWKELAT- 1383

Query: 1303 IFDCCYLTS----KLSRGGTYTFRTACVSKAGMGPYSSPSEQVLLGGPSHLAS------- 1351
                C  TS       L    Y FR   ++   G    S  SE   +G
Sbjct: 1384 ----CRSTSFNVQDLLPDHEYKFRVRAINVYGTSEPSQESELTTVGEKPEEPKMKWRCQT 1439

Query: 1352 ----EEESQGRSAQPLPSTKTFAF---QTQIQRGRFSVVRQCWEKASGRALAAKIIP-YH 1403
                 E E   R+       K  F      +  ++  G+F V +  EK + +  AK    Y
Sbjct: 1440 DDEKEPEVDYRTVTINTEQKVSDFYDIEERLGSGKFGQVFRLVEKKTRKVWAGKFFKAYS 1499

Query: 1404 PKDKTAVLREYEALKGLRHPHLAQLHAAYLSPRHLVLILELCSGPELLP-CLAERASYSE 1462
             K+K  + +E +    L HP L Q    A+     ++V++LE+ SG EL    + E    +E
Sbjct: 1500 AKEKENIRQEISIMNCLHHPKLVQCVDAFEEKANIVMVLEIVSGGELFERIIDEDFELTE 1559

Query: 1463 SEVKDYLWQMLSATQYLHNQHILHLDLRSENMIITEY--NLLKVVDLGNAQSLSQE---K 1517
                E   Y+ Q+       +Y+H Q I+HLDL+ EN++           +K++D G A+ L      K
Sbjct: 1560 RECIKYMRQISEGVEYIHKQGIVHLDLKPENIMCVNKTGTRIKLIDFGLARRLENAGSLK 1619

Query: 1518 VLPSDKFKDYLETMAPELLEGQGAVPQTDIWAIGVTAFIMLSAEYPVSSEGARDLQRGLR 1577
             VL        E +APE++  +         TD+W+IGV  +I++S   P  +         +
Sbjct: 1620 VLFGTP-----EFVAPEVINYEPISYATDMWSIGVICYILVSGLSPFMGDNDNETLANVT 1674

Query: 1578 KGLVRL-SRCYAGLSGGAVAFLRSTLCAQPWGRPCASSCLQCPWLTEE 1624
             +   +S  A F++ + L       R  + CLQ  PWL ++
Sbjct: 1675 SATWDFDDEAFDEISDDAKDFISNLLKKDMKNRLDCTQCLQHPWLMKD 1722    (SEQ ID NO:19)

Score = 64.4 bits (154), Expect = 9e-09
 Identities = 36/106 (33%), Positives = 52/106 (48%), Gaps = 4/106 (3%)

Query: 54   PSMQVTIEDVQAQTGGTAQFEAIIEGDPQPSVTWYKDSVQLVDSTRLS-QQQEGTTYSLV 112
             P    TI D++    G   A+F+   IEG P P V W+KD   + +S     E      SL+
Sbjct: 1808 PYFSKTIRDLEVVEGSAARFDCKIEGYPDPEVVWFKDDQSIRESRHFQIDYDEDGNCSLI 1867

Query: 113  LRHVASKDAGVYTCLAQNTGGQVLCKAELLV---LGGDNEPDSEKQ 155
             +     V     D  YTC A N+ G+  C  AEL+V       G+ E    E++
Sbjct: 1868 ISDVCGDDDAKYTCKAVNSLGEATCTAELIVETMEEGEGEGEEEEE 1913    (SEQ ID NO:20)

Score = 64.0 bits (153), Expect = 1e-08
 Identities = 35/96 (36%), Positives = 46/96 (47%)

Query: 53   PPSMQVTIEDVQAQTGGTAQFEAIIEGDPQPSVTWYKDSVQLVDSTRLSQQQEGTTYSLV 112
             PP     + V   G  +F   I G PQP VTW K  +V L  S R+S ++           L
Sbjct: 160  PPKFATKLGRVVVKEGQMGRFSCKITGRPQPQVTWLKGNVPLQPSARVSVSEKNGMQVLE 219

Query: 113  LRHVASKDAGVYTCLAQNTGGQVLCKAELLVLGGDN 148
              +  V     D GVYTCL  N  G+       AEL + G D+
Sbjct: 220  IHGVNQDDVGVYTCLVVNGSGKASMSAELSIQGLDS 255    (SEQ ID NO:21)

Score = 59.3 bits (141), Expect = 3e-07
 Identities = 30/100 (30%), Positives = 50/100 (50%), Gaps = 3/100 (3%)

Query: 47   LPALPGPPSMQVTIE---DVQAQTGGTAQFEAIIEGDPQPSVTWYKDSVQLVDSTRLSQQ 103
             LP  P   P+   +   D++    G       + G+P  PV W   ++   +S        +
Sbjct: 613  LPVAPSKPTAPIFLQGLSDLKVMDGSQVTMTVQVSGNPPPEVIWLHNGNEIQESEDFHFE 672

Query: 104  QEGTTYSLVLRHVASKDAGVYTCLAQNTGGQVLCKAELLV 143
             Q GT +SL ++ V +D G YTC A N+ G+V  +A L V
Sbjct: 673  QRGTQHSLWIQEVFPEDTGTYTCEAWNSAGEVRTQAVLTV 712    (SEQ ID NO:22)
```

FIGURE 2I

```
Score = 57.4 bits (136), Expect = 1e-06
Identities = 32/89 (35%), Positives = 46/89 (50%), Gaps = 1/89 (1%)

Query: 1160 PTFLRELSDETVVLGQSVTLACQVSAQPAAQATWSKDGAPLESSSRVLISATLKNFQLLT 1219
             P F +L   V GQ   +C+++ +P Q TW K   PL+ S+RV +S     Q+L
Sbjct: 161  PKFATKLGRVVVKEGQMGRFSCKITGRPQPQVTWLKGNVPLQPSARVSVSEK-NGMQVLE 219

Query: 1220 ILVVVAEDLGVYTCSVSNALGTVTTTGVL 1248
             I  V +D+GVYTC V N  G  + + L
Sbjct: 220  IHGVNQDDVGVYTCLVVNGSGKASMSAEL 248    (SEQ ID NO:23)

Score = 53.5 bits (126), Expect = 2e-05
Identities = 32/98 (32%), Positives = 46/98 (46%), Gaps = 4/98 (4%)

Query: 1159 APTFLRELSDETVVLGQSVTLACQVSAQPAAQATWSKDGAPLESSSRVLISATLKNFQLL 1218
             AP+F   L D V+ GQ    L C V   P + TW  +G P++ +      +    +  L
Sbjct: 513  APSFSSVLKDCAVIEGQDFVLQCSVRGTPVPRITWLLNGQPIQYARSTCEAGVAE----L 568

Query: 1219 TILVVVAEDLGVYTCSVSNALGTVTTTGVLRKAERPSS 1256
              I  + ED G YTC  NALG V+ + +  E+ SS
Sbjct: 569  HIQDALPEDHGTYTCLAENALGQVSCSAWVTVHEKKSS 606    (SEQ ID NO:24)

Score = 53.1 bits (125), Expect = 2e-05
Identities = 37/113 (32%), Positives = 48/113 (41%), Gaps = 1/113 (0%)

Query: 1140 RKKPGLASFRLSGLKSWDRAPTFLRELSDETVVLGQSVTLACQVSAQPAAQATWSKDGAP 1199
             +K   + +L   S   AP FL+ LSD V+ G  VT+ QVS P + W +G
Sbjct: 603  KKSSRKSEYLLPVAPSKPTAPIFLQGLSDLKVMDGSQVTMTVQVSGNPPPEVIWLHNGNE 662

Query: 1200 LESSSSRVLISATLKNFQLLTILVVVAEDLGVYTCSVSNALGTVTTTGVLRKAE 1252
             ++ S          L I V  ED G YTC   N+ G VT  VL   E
Sbjct: 663  IQESEDFHFEQRGTQHS-LWIQEVFPEDTGTYTCEAWNSAGEVRTQAVLTVQE 714    (SEQ ID NO:25)

Score = 51.9 bits (122), Expect = 5e-05
Identities = 34/101 (33%), Positives = 50/101 (48%), Gaps = 2/101 (1%)

Query: 46   SLPALPGPPSMQVTIEDVQAQTGGTAQFEAIIEGDPQPSVTWYKDSVQLVDSTR-LSQQQ 104
             S+P L   P+  +   ++  + G TA+FE  + G P+P VTW+++   +    R L
Sbjct: 26   SMP-LTEAPAFILPPRNLCIKEGATAKFEGRVRGYPEPQVTWHRNGQPITSGGRFLLDCG 84

Query: 105  EGTTYSLVLRHVASKDAGVYTCLAQNTGGQVLCKAELLVLG 145
              T+SLV+  V  +D G YTC A N  G     EL V G
Sbjct: 85   IRGTFSLVIHAVHEEDRGKYTCEATNGSGARQVTVELTVEG 125    (SEQ ID NO:26)

Score = 50.8 bits (119), Expect = 1e-04
Identities = 41/182 (22%), Positives = 65/182 (35%), Gaps = 26/182 (14%)

Query: 1130 PEGLEKEGPPRKKPGLASFRLSGLKSWDRA------------------PTFLRELSDETV 1171
             P G E++ P   +P  R  GL S D             P F  +   + V
Sbjct: 366  PSGEERKRPAPPRPATFPTRQPGLGSQDVVSKAANRRIPMEGQRDSAFPKFESKPQSQEV 425

Query: 1172 VLGQSVTLACQVSAQPAAQATWSKDGAPLESSSRVLISATLKNFQLLTILVVVAEDLGVY 1231
              Q+V  C+VS P +  W +G P+    +         L +L      D G Y
Sbjct: 426  KENQTVKFRCEVSGIPKPEVAWFLEGTPVRRQEGSIEVYEDAGSHYLCLLKARTRDSGTY 485

Query: 1232 TCSVSNALGTVTTTGVLRKAERPSSSPCPDIGEVYADGVLLVWKPVESYGPVTYIVQCSL 1291
             +C+ SNA G V+ + L+     P   V D ++ +     +++QCS+
Sbjct: 486  SCTASNAQGQVSCSWTLQVERLAVMEVAPSFSSVLKDCAVIEGQ--------DFVLQCSV 537

Query: 1292 EG 1293
              G
Sbjct: 538  RG 539    (SEQ ID NO:27)

Score = 50.4 bits (118), Expect = 2e-04
Identities = 26/100 (26%), Positives = 47/100 (47%), Gaps = 3/100 (3%)
```

FIGURE 2J

```
Query:   54  PSMQVTIEDVQAQTGGTAQFEAIIEGDPQPSVTWYKDSVQLVDSTRLSQQQEGTTYSLVL  113
             P+ + ++DV   G      + + DP ++ W  + L +  +  QEG+ S+ +
Sbjct: 1098  PAFKQKLQDVHVAEGKKLLLQCQVSSDPPATIIWTLNGKTLKTTKFIILSQEGSLCSVSI 1157

Query:  114  RHVASKDAGVYTCLAQNTGGQVLCKAELLVLGGDNEPDSE  153
                +D G+Y C+A+N  GQ  C  ++ V   D+ P SE
Sbjct: 1158  EKALLEDRGLYKCVAKNDAGQAECSCQVTV---DDAPASE 1194  (SEQ ID NO:28)

Score =  50.0 bits (117), Expect = 2e-04
 Identities = 35/125 (28%), Positives = 59/125 (47%), Gaps = 16/125 (12%)

Query: 1154  KSWDRAPTFLRELSDETVVLGQSVTLACQVSAQPAAQATWSKDGAPLESSSRVLISATLK 1213
             +S   AP F ++L D V G+ + L CQVS+ P A   W+ +G L+++  +++S
Sbjct: 1092  ESQGTAPAFKQKLQDVHVAEGKKLLLQCQVSSDPPATIIWTLNGKTLKTTKFIILSQE-G 1150

Query: 1214  NFQLLTILVVVAEDLGVYTC---------------SVSNALGTVTTTGVLRKAERPSSSP 1258
             +    ++I + ED G+Y C               +V +A + T    K+ RP SS
Sbjct: 1151  SLCSVSIEKALLEDRGLYKCVAKNDAGQAECSCQVTVDDAPASENTKAPEMKSRRPKSSL 1210

Query: 1259  CPDIG 1263
             P +G
Sbjct: 1211  PPVLG 1215  (SEQ ID NO:29)

Score =  48.0 bits (112), Expect = 8e-04
 Identities = 26/87 (29%), Positives = 38/87 (42%)

Query: 1159  APTFLRELSDETVVLGQSVTLACQVSAQPAAQATWSKDGAPLESSSRVLISATLKNFQLL 1218
             AP F+    +  + G+     +V  P   Q TW ++G P+ S  R L+    ++   L
Sbjct:   32  APAFILPPRNLCIKEGATAKFEGRVRGYPEPQVTWHRNGQPITSGGRFLLDCGIRGTFSL  91

Query: 1219  TILVVVAEDLGVYTCSVSNALGTVTTT 1245
                I V  ED G YTC +N G  T
Sbjct:   92  VIHAVHEEDRGKYTCEATNGSGARQVT 118  (SEQ ID NO:30)

Score =  45.3 bits (105), Expect = 0.005
 Identities = 37/140 (26%), Positives = 54/140 (38%), Gaps = 23/140 (16%)

Query:   22  TNHPSMVGCGWHPGLCGWGGGLHSSLPALPGPPSMQVTIEDVQAQTGGTAQFEAIIEGDP  81
             +N    V C W +          L + PS  ++D   G   +   + G P
Sbjct:  490  SNAQGQVSCSWTLQV--------ERLAVMEVAPSFSSVLKDCAVIEGQDFVLQCSVRGTP 541

Query:   82  QPSVTWYKDS--VQLVDSTRLSQQQEGTTYSLVLRHVASKDAGVYTCLAQNTGGQVLCKA 139
             P +TW +  +Q  ST    E    L ++    +D G YTCLA+N  GQV C A
Sbjct:  542  VPRITWLLNGQPIQYARSTC-----EAGVAELHIQDALPEDHGTYTCLAENALGQVSCSA 596

Query:  140  ELLVLGGDNEPDSEKQSHRR 159
              + V        EK+S R+
Sbjct:  597  WVTV--------HEKKSSRK 608  (SEQ ID NO:31)

Score =  44.5 bits (103), Expect = 0.009
 Identities = 26/104 (25%), Positives = 44/104 (42%), Gaps = 7/104 (6%)

Query:   41  GGLHSSLPALPGPPSMQVTIEDVQAQTGGTAQFEAIIEGDPQPSVTWYKDSVQLV-DSTR  99
             G   S+ P    P Q      + + T +F  + G P+P V W+ +   +
Sbjct:  407  GQRDSAFPKFESKPQSQ------EVKENQTVKFRCEVSGIPKPEVAWFLEGTPVRRQEGS 460

Query:  100  LSQQQEGTTYSLVLRHVASKDAGVYTCLAQNTGGQVLCKAELLV 143
                + ++  ++ L L  ++D+G Y+C A N GQV C   L V
Sbjct:  461  IEVYEDAGSHYLCLLKARTDSGTYSCTASNAQGQVSCSWTLQV  504  (SEQ ID NO:32)

Score =  44.1 bits (102), Expect = 0.012
 Identities = 26/82 (31%), Positives = 38/82 (45%), Gaps = 1/82 (1%)

Query:   63  VQAQTGGTAQFEAIIEGDPQPSVTWYKDSVQLV-DSTRLSQQQEGTTYSLVLRHVASKDA 121
```

FIGURE 2K

```
              V A  G +       I GDP P+V W +D   L  D+      Q    ++LVL+ V    A
Sbjct: 730  VTASLGQSVLISCAIAGDPFPTVHWLRDGKALCKDTGHFEVLQNEDVFTLVLKKVQPWHA 789

Query: 122  GVYTCLAQNTGGQVLCKAELLV 143
            G Y  L +N  G+   C+  L++
Sbjct: 790  GQYEILLKNRVGECSCQVSLML 811    (SEQ ID NO:33)

Score = 43.8 bits (101), Expect = 0.015
 Identities = 26/89 (29%), Positives = 35/89 (39%)

Query: 1160 PTFLRELSDETVVLGQSVTLACQVSAQPAAQATWSKDGAPLESSSRVLISATLKNFQLLT 1219
            P F + + D  VV G +    C++   P +   W KD  +  S    I       L
Sbjct: 1808 PYFSKTIRDLEVVEGSAARFDCKIEGYPDPEVVWFKDDQSIRESRHFQIDYDEDGNCSLI 1867

Query: 1220 ILVVVAEDLGVYTCSVSNALGTVTTTGVL 1248
            I  V +D   YTC   N+LG  T T  L
Sbjct: 1868 ISDVCGDDDAKYTCKAVNSLGEATCTAEL 1896  (SEQ ID NO:34)
```

FIGURE 2L

```
   1 CAGCACGAGG AACTCCTTCT GATCACCTGG CCAGCTGAGG TCAGAGTGGG
  51 AGAGGCAGTG GTTCCATTGA AGGAGTACTC CTAACTGTCA GAAGCCTGGG
 101 CGGTCAGGAT GGGGTGCTGT CGCTTGGGCT GCGGGGGGTG TTCAGTTGCC
 151 CACAGTGTAT CTCAGGGTCT CACCAACCAT CCAAGCATGG TAGGCTGTGG
 201 CTGGCACCCA GGGTTGTGTG GCTGGGGAGG TGGTCTCCAC AGTTCCCTCC
 251 CTGCCCTCCC AGGGCCCCCA TCCATGCAGG TAACCATCGA GGATGTGCAG
 301 GCACAGACAG GCGGAACGGC CCAATTCGAG GCTATCATTG AGGGCGACCC
 351 ACAGCCCTCG GTGACCTGGT ACAAGGACAG CGTCCAGCTG GTGGACAGCA
 401 CCCGGCTTAG CCAGCAGCAA GAAGGCACCA CATACTCCCT GGTGCTGAGG
 451 CATGTGGCCT CGAAGGATGC CGGCGTTTAC ACCTGCCTGG CCCAAAACAC
 501 TGGTGGCCAG GTGCTCTGCA AGGCAGAGCT GCTGGTGCTT GGGGGGGACA
 551 ATGAGCCGGA CTCAGAGAAG CAAAGCCACC GGAGGAAGCT GCACTCCTTC
 601 TATGAGGTCA AGGAGGAGAT TGGAAGGGGC GTGTTTGGCT TCGTAAAAAG
 651 AGTGCAGCAC AAAGGAAACA AGATCTTGTG CGCTGCCAAG TTCATCCCCC
 701 TACGGAGCAG AACTCGGGCC CAGGCATACA GGGAGCGAGA CATCCTGGCC
 751 GCGCTGAGCC ACCCGCTGGT CACGGGGCTG CTGGACCAGT TTGAGACCCG
 801 CAAGACCCTC ATCCTCATCC TGGAGCTGTG CTCATCCGAG GAGCTGCTGG
 851 ACCGCCTGTA CAGGAAGGGC GTGGTGACGG AGGCCGAGGT CAAGGTCTAC
 901 ATCCAGCAGC TGGTGGAGGG GCTGCACTAC CTGCACAGCC ATGGCGTTCT
 951 CCACCTGGAC ATAAAGCCCT CTAACATCCT GATGGTGCAT CCTGCCCGGG
1001 AAGACATTAA AATCTGCGAC TTTGGCTTTG CCCAGAACAT CACCCCAGCA
1051 GAGCTGCAGT TCAGCCAGTA CGGCTCCCCT GAGTTCGTCT CCCCCGAGAT
1101 CATCCAGCAG AACCCTGTGA GCGAAGCCTC CGACATTTGG GCCATGGGTG
1151 TCATCTCCTA CCTCAGCCTG ACCTGCTCAT CCCCATTTGC CGGCGAGAGT
1201 GACCGTGCCA CCCTCCTGAA CGTCCTGGAG GGGCGCGTGT CATGGAGCAG
1251 CCCCATGGCT GCCCACCTCA GCGAAGACGC CAAAGACTTC ATCAAGGCTA
1301 CGCTGCAGAG AGCCCCTCAG GCCCGGCCTA GTGCGGCCCA GTGCCTCTCC
1351 CACCCCTGGT TCCTGAAATC CATGCCTGCG GAGGAGGCCC ACTTCATCAA
1401 CACCAAGCAG CTCAAGTTCC TCCTGGCCCG AAGTGCTGG CAGCGTTCCC
1451 TGATGAGCTA CAAGTCCATC CTGGTGATGC GCTCCATCCC TGAGCTGCTG
1501 CGGGGCCCAC CCGACAGCCC CTCCCTCGGC GTAGCCCGGC ACCTCTGCAG
1551 GGACACTGGT GGCTCCTCCA GTTCCTCCTC CTCCTCTGAC AACGAGCTCG
1601 CCCCATTTGC CCGGGCTAAG TCACTGCCAC CCTCCCCGGT GACACACTCA
1651 CCACTGCTGC ACCCCCGGGG CTTCCTGCGG CCCTCGGCCA GCCTGCCTGA
1701 GGAAGCCGAG GCCAGTGAGC GCTCCACCGA GGCCCCAGCT CCGCCTGCAT
1751 CTCCCGAGGG TGCCGGGCCA CCGGCCGCCC AGGGCTGCGT GCCCCGGCAC
1801 AGCGTCATCC GCAGCCTGTT CTACCACCAG GCGGGTGAGA GCCCTGAGCA
1851 CGGGGCCCTG GCCCCGGGGA GCAGGCGGCA CCCGGCCCGG CGGCGGCACC
1901 TGCTGAAGGG CGGCTACATT GCGGGGGCGC TGCCAGGCCT GCGCGAGCCA
1951 CTGATGGAGC ACCGCGTGCT GGAGGAGGAG GCCGCCAGGG AGGAGCAGGC
2001 CACCCTCCTG GCCAAAGCCC CCTCATTCGA GACTGCCCTC CGGCTGCCTG
2051 CCTCTGGCAC CCACTTGGCC CCTGGCCACA GCCACTCCCT GGAACATGAC
2101 TCTCCGAGCA CCCCCCGCCC CTCCTCGGAG GCCTGCGGTG AGGCACAGCG
2151 ACTGCCTTCA GCCCCCTCCG GGGGGGCCCC TATCAGGGAC ATGGGGCACC
2201 CTCAGGGCTC CAAGCAGCTT CCATCCACTG GTGGCCACCC AGGCACTGCT
2251 CAGCCAGAGA GGCCATCCCC GGACAGCCCT TGGGGCAGC CAGCCCCTTT
2301 CTGCCACCCC AAGCAGGGTT CTGCCCCCCA GGAGGGCTGC AGCCCCCACC
2351 CAGCAGTTGC CCCATGCCCT CCTGGCTCCT TCCCTCCAGG ATCTTGCAAA
2401 GAGGCCCCCT TAGTACCCTC AAGCCCCTTC TTGGGACAGC CCCAGGCACC
2451 CCCTGCCCCT GCCAAAGCAA GCCCCCCATT GGACTCTAAG ATGGGGCCTG
2501 GAGACATCTC TCTTCCTGGG AGGCCAAAAC CCGGCCCCTG CAGTTCCCCA
2551 GGGTCAGCCT CCCAGGCGAG CTCTTCCCAA GTGAGCTCCC TCAGGGTGGG
2601 CTCCTCCCAG GTGGGCACAG AGCCTGGCCC CTCCCTGGAT GCGGAGGGCT
2651 GGACCCAGGA GGCTGAGGAT CTGTCCGACT CCACACCCAC CTTGCAGCGG
2701 CCTCAGGAAC AGGTGACCAT GCGCAAGTTC TCCCTGGGTG GTCGCGGGGG
2751 CTACGCAGGC GTGGCTGGCC ATGGCACCTT TGCCTTTGGT GGAGATGCAG
2801 GGGGCATGCT GGGGCAGGGG CCCATGTGGG CCAGGATAGC CTGGGCTGTG
2851 TCCCAGTCGG AGGAGGAGGA GCAGGAGGAG GCCAGGGCTG AGTCCCAGTC
2901 GGAGGAGCAG CAGGAGGCCA GGGCTGAGAG CCCACTGCCC CAGGTCAGTG
2951 CAAGGCCTGT GCCTGAGGTC GGCAGGGCTC CCACCAGGAG CTCTCCAGAG
3001 CCCACCCCAT GGGAGGACAT CGGGCAGGTC TCCCTGGTGC AGATCCGGGA
3051 CCTGTCAGGT GATGCGGAGG CGGCCGACAC AATATCCCTG GACATTTCCG
3101 AGGTGGACCC CGCCTACCTC AACCTCTCAG ACCTGTACGA TATCAAGTAC
3151 CTCCCATTCG AGTTTATGAT CTTCAGGAAA GTCCCCAAGT CCGCTCAGCC
3201 AGAGCCGCCC TCCCCCATGG CTGAGGAGGA GCTGGCCGAG TTCCGGAGCC
3251 CCACGTGGCC CTGGCCAGGT GAACTGGGCC CCACGCAGG CCTGGAGATC
3301 ACAGAGGAGT CAGAGGATGT GGACGCGCTG TGGCAGAGG CTGCCGTGGG
3351 CAGGAAGCGC AAGTGGTCCT CGCCGTCACG CAGCCTCTTC CACTTCCCTG
3401 GGAGGCACCT GCCGCTGGAT GAGCCTGCAG AGCTGGGGCT GCGTGAGAGA
3451 GTGAAGGCCT CCGTGGAGCA CATCTCCCGG ATCCTGAAGG CAGGCCGGA
```

FIGURE 3A

```
3501 AGGTCTGGAG AAGGAGGGGC CCCCCAGGAA GAAGCCAGGC CTTGCTTCCT
3551 TCCGGCTCTC AGGTCTGAAG AGCTGGGACC GAGCGCCGAC ATTCCTAAGG
3601 GAGCTCTCAG ATGAGACTGT GGTCCTGGGC CAGTCAGTGA CACTGGCCTG
3651 CCAGGTGTCA GCCCAGCCAG CTGCCCAGGC CACCTGGAGC AAAGACGGAG
3701 CCCCCCTGGA GAGCAGCAGC CGTGTCCTCA TCTCTGCCAC CCTCAAGAAC
3751 TTCCAGCTTC TGACCATCCT GGTGGTGGTG GCTGAGGACC TGGGTGTGTA
3801 CACCTGCAGC GTGAGCAATG CGCTGGGGAC AGTGACCACC ACGGGCGTCC
3851 TCCGGAAGGC AGAGCGCCCC TCATCTTCGC CATGCCCGGA TATCGGGGAG
3901 GTGTACGCGG ATGGGGTGCT GCTGGTCTGG AAGCCCGTGG AATCCTACGG
3951 CCCTGTGACC TACATTGTGC AGTGCAGCCT AGAAGGCGGC AGCTGGACCA
4001 CACTGGCCTC CGACATCTTT GACTGCTGCT ACCTGACCAG CAAGCTCTCC
4051 CGGGGTGGCA CCTACACCTT CCGCACGGCA TGTGTCAGCA AGGCAGGAAT
4101 GGGTCCCTAC AGCAGCCCCT CGGAGCAAGT CCTCCTGGGA GGGCCCAGCC
4151 ACCTGGCCTC TGAGGAGGAG AGCCAGGGGC GGTCAGCCCA ACCCCTGCCC
4201 AGCACAAAGA CCTTCGCATT CCAGACACAG ATCCAGAGGG GCCGCTTCAG
4251 CGTGGTGCGG CAATGCTGGG AGAAGGCCAG CGGGCGGGCG CTGGCCGCCA
4301 AGATCATCCC CTACCACCCC AAGGACAAGA CAGCAGTGCT GCGCGAATAC
4351 GAGGCCCTCA AGGGCCTGCG CCACCCGCAC CTGGCCCAGC TGCACGCAGC
4401 CTACCTCAGC CCCCGGCACC TGGTGCTCAT CTTGGAGCTG TGCTCTGGGC
4451 CCGAGCTGCT CCCCTGCCTG GCCGAGAGGG CCTCCTACTC AGAATCTGAG
4501 GTGAAGGACT ACCTGTGGCA GATGTTGAGT GCCACCCAGT ACCTGCACAA
4551 CCAGCACATC CTGCACCTGG ACCTGAGGTC CGAGAACATG ATCATCACCG
4601 AATACAACCT GCTCAAGGTC GTGGACCTGG GCAATGCACA GAGCCTCAGC
4651 CAGGAGAAGG TGCTGCCCTC AGACAAGTTC AAGGACTACC TAGAGACCAT
4701 GGCTCCAGAG CTCCTGGAGG GCCAGGGGGC TGTTCCACAG ACAGACATCT
4751 GGGCCATCGG TGTGACAGCC TTCATCATGC TGAGCGCCGA GTACCCGGTG
4801 AGCAGCGAGG GTGCACGCGA CCTGCAGAGA GGACTGCGCA AGGGGCTGGT
4851 CCGGCTGAGC CGCTGCTACG CGGGGCTGTC CGGGGCGCC GTGGCCTTCC
4901 TGCGCAGCAC TCTGTGCGCC CAGCCCTGGG GCCGGCCCTG CGCGTCCAGC
4951 TGCCTGCAGT GCCCGTGGCT AACAGAGGAG GGCCCGGCCT GTTCGCGGCC
5001 CGCGCCCGTG ACCTTCCCTA CCGCGCGGCT GCGCGTCTTC GTGCGCAATC
5051 GCGAGAAGAG ACGCGCGCTG CTGTACAAGA GGCACAACCT GGCCCAGGTG
5101 CGCTGAGGGT CGCCCCGGCC ACACCCTTGG TCTCCCCGCT GGGGGTCGCT
5151 GCAGACGCGC CAATAAAAAC GCACAGCCGG GCGAGAAAAA AAAAAAAAAA
5201 AAAAAAA (SEQ ID NO:3)
```

FEATURES:
Start:    109
Exon:     109-5103
Stop:     5104

SNPs:

| DNA Position | Major | Minor | Domain | Protein Position | Major | Minor |
|---|---|---|---|---|---|---|
| 311 | T | C G | Exon | 68 | V | A G |
| 1741 | C | T | Exon | 545 | P | S |
| 2714 | T | C | Exon | 869 | V | A |
| 2745 | C | T | Exon | 879 | R | R |
| 2859 | A | G | Exon | 917 | S | S |
| 3420 | T | C | Exon | 1104 | D | D |

Context:

DNA
Position

311    AACTCCTTCTGATCACCTGGCCAGCTGAGGTCAGAGTGGGAGAGGCAGTGGTTCCATTGA
       AGGAGTACTCCTAACTGTCAGAAGCCTGGGCGGTCAGGATGGGGTGCTGTCGCTTGGGCT
       GCGGGGGGTGTTCAGTTGCCCACAGTGTATCTCAGGGTCTCACCAACCATCCAAGCATGG
       TAGGCTGTGGCTGGCACCCAGGGTTGTGTGGCTGGGGAGGTGGTCTCCACAGTTCCCTCC
       CTGCCCTCCCAGGGCCCCCATCCATGCAGGTAACCATCGAGGATGTGCAGGCACAGACAG
       [T,C,G]
       CGGAACGGCCCAATTCGAGGCTATCATTGAGGGCGACCCACAGCCCTCGGTGACCTGGTA
       CAAGGACAGCGTCCAGCTGGTGGACAGCACCCGGCTTAGCCAGCAGCAAGAAGGCACCAC
       ATACTCCCTGGTGCTGAGGCATGTGGCCTCGAAGGATGCCGGCGTTTACACCTGCCTGGC
       CCAAAACACTGGTGGCCAGGTGCTCTGCAAGGCAGAGCTGCTGGTGCTTGGGGGGACAA
       TGAGCCGGACTCAGAGAAGCAAAGCCACCGGAGGAAGCTGCACTCCTTCTATGAGGTCAA

FIGURE 3B

| | |
|---|---|
| 1741 | CAGCGTTCCCTGATGAGCTACAAGTCCATCCTGGTGATGCGCTCCATCCCTGAGCTGCTG |
| | CGGGGCCCACCCGACAGCCCCTCCCTCGGCGTAGCCCGGCACCTCTGCAGGGACACTGGT |
| | GGCTCCTCCAGTTCCTCCTCCTCCTCTGACAACGAGCTCGCCCCATTTGCCCGGGCTAAG |
| | TCACTGCCACCCTCCCCGGTGACACACTCACCACTGCTGCACCCCCGGGGCTTCCTGCGG |
| | CCCTCGGCCAGCCTGCCTGAGGAAGCCGAGGCCAGTGAGCGCTCCACCGAGGCCCCAGCT |
| | [C,T] |
| | CGCCTGCATCTCCCGAGGGTGCCGGGCCACCGGCCGCCCAGGGCTGCGTGCCCCGGCACA |
| | GCGTCATCCGCAGCCTGTTCTACCACCAGGCGGGTGAGAGCCCTGAGCACGGGGCCCTGG |
| | CCCCGGGGAGCAGGCGGCACCCGGCCCGGCGGCGGCCACCTGCTGAAGGGCGGCTACATTG |
| | CGGGGGCGCTGCCAGGCCTGCGCGAGCCACTGATGGAGCACCGCGTGCTGGAGGAGGAGG |
| | CCGCCAGGGAGGAGCAGGCCACCCTCCTGGCCAAAGCCCCCTCATTCGAGACTGCCCTCC |
| 2714 | TACCCTCAAGCCCCTTCTTGGGACAGCCCCAGGCACCCCCTGCCCCTGCCAAAGCAAGCC |
| | CCCCATTGGACTCTAAGATGGGGCCTGGAGACATCTCTCTTCCTGGGAGGCCAAAACCCG |
| | GCCCCTGCAGTTCCCCAGGGTCAGCCTCCCAGGCGAGCTCTTCCCAAGTGAGCTCCCTCA |
| | GGGTGGGCTCCTCCCAGGTGGGCACAGAGCCTGGCCCCTCCCTGGATGCGGAGGGCTGGA |
| | CCCAGGAGGCTGAGGATCTGTCCGACTCCACACCCACCTTGCAGCGGCCTCAGGAACAGG |
| | [T,C] |
| | GACCATGCGCAAGTTCTCCCTGGGTGGTCGCGGGGGCTACGCAGGCGTGGCTGGCTATGG |
| | CACCTTTGCCTTTGGTGGAGATGCAGGGGGCATGCTGGGGCAGGGGCCCATGTGGGCCAG |
| | GATAGCCTGGGCTGTGTCCCAGTCGGAGGAGGAGGAGCAGGAGGAGGCCAGGGCTGAGTC |
| | CCAGTCGGAGGAGCAGCAGGAGGCCAGGGCTGAGAGCCCACTGCCCCAGGTCAGTGCAAG |
| | GCCTGTGCCTGAGGTCGGCAGGGCTCCCACCAGGAGCTCTCCAGAGCCCACCCCATGGGA |
| 2745 | GGCACCCCCTGCCCCTGCCAAAGCAAGCCCCCCATTGGACTCTAAGATGGGGCCTGGAGA |
| | CATCTCTCTTCCTGGGAGGCCAAAACCCGGCCCCTGCAGTTCCCCAGGGTCAGCCTCCCA |
| | GGCGAGCTCTTCCCAAGTGAGCTCCCTCAGGGTGGGCTCCTCCCAGGTGGGCACAGAGCC |
| | TGGCCCCTCCCTGGATGCGGAGGGCTGGACCCAGGAGGCTGAGGATCTGTCCGACTCCAC |
| | ACCCACCTTGCAGCGGCCTCAGGAACAGGTGACCATGCGCAAGTTCTCCCTGGGTGGTCG |
| | [C,T] |
| | GGGGGCTACGCAGGCGTGGCTGGCTATGGCACCTTTGCCTTTGGTGGAGATGCAGGGGGC |
| | ATGCTGGGGCAGGGGCCCATGTGGGCCAGGATAGCCTGGGCTGTGTCCCAGTCGGAGGAG |
| | GAGGAGCAGGAGGAGGCCAGGGCTGAGTCCCAGTCGGAGGAGCAGCAGGAGGCCAGGGCT |
| | GAGAGCCCACTGCCCCAGGTCAGTGCAAGGCCTGTGCCTGAGGTCGGCAGGGCTCCCACC |
| | AGGAGCTCTCCAGAGCCCACCCCATGGGAGGACATCGGGCAGGTCTCCCTGGTGCAGATC |
| 2859 | CTCCCAGGCGAGCTCTTCCCAAGTGAGCTCCCTCAGGGTGGGCTCCTCCCAGGTGGGCAC |
| | AGAGCCTGGCCCCTCCCTGGATGCGGAGGGCTGGACCCAGGAGGCTGAGGATCTGTCCGA |
| | CTCCACACCCACCTTGCAGCGGCCTCAGGAACAGGTGACCATGCGCAAGTTCTCCCTGGG |
| | TGGTCGCGGGGGCTACGCAGGCGTGGCTGGCTATGGCACCTTTGCCTTTGGTGGAGATGC |
| | AGGGGGCATGCTGGGGCAGGGGCCCATGTGGGCCAGGATAGCCTGGGCTGTGTCCCAGTC |
| | [A,G] |
| | GAGGAGGAGGAGCAGGAGGAGGCCAGGGCTGAGTCCCAGTCGGAGGAGCAGCAGGAGGCC |
| | AGGGCTGAGAGCCCACTGCCCCAGGTCAGTGCAAGGCCTGTGCCTGAGGTCGGCAGGGCT |
| | CCCACCAGGAGCTCTCCAGAGCCCACCCCATGGGAGGACATCGGGCAGGTCTCCCTGGTG |
| | CAGATCCGGGACCTGTCAGGTGATGCGGAGGCGGCCGACACAATATCCCTGGACATTTCC |
| | GAGGTGGACCCCGCCTACCTCAACCTCTCAGACCTGTACGATATCAAGTACCTCCCATTC |
| 3420 | CAACCTCTCAGACCTGTACGATATCAAGTACCTCCCATTCGAGTTTATGATCTTCAGGAA |
| | AGTCCCCAAGTCCGCTCAGCCAGAGCCGCCCTCCCCCATGGCTGAGGAGGAGCTGGCCGA |
| | GTTCCCGGAGCCCACGTGGCCCTGGCCAGGTGAACTGGGCCCCACGCAGGCCTGGAGAT |
| | CACAGAGGAGTCAGAGGATGTGGACGCGCTGCTGGCAGAGGCTGCCGTGGGCAGGAAGCG |
| | CAAGTGGTCCTCGCCGTCACGCAGCCTCTTCCACTTCCCTGGGAGGCACCTGCCGCTGGA |
| | [T,C] |
| | GAGCCTGCAGAGCTGGGGCTGCGTGAGAGAGTGAAGGCCTCCGTGGAGCACATCTCCCGG |
| | ATCCTGAAGGGCAGGCCGGAAGGTCTGGAGAAGGAGGGGCCCCCCAGGAAGAAGCCAGGC |
| | CTTGCTTCCTTCCGGCTCTCAGGTCTGAAGAGCTGGGACCGAGCGCCGACATTCCTAAGG |
| | GAGCTCTCAGATGAGACTGTGGTCCTGGGCCAGTCAGTGACACTGGCCTGCCAGGTGTCA |
| | GCCCAGCCAGCTGCCCAGGCCACCTGGAGCAAAGACGGAGCCCCCTGGAGAGCAGCAGC |

Chromosome map position: 1

Bac accession number: AC023889

FIGURE 3C

SEQUENCE LISTING

<160> NUMBER OF SEQ ID NOS: 34

<210> SEQ ID NO 1
<211> LENGTH: 5207
<212> TYPE: DNA
<213> ORGANISM: Human

<400> SEQUENCE: 1

| | | | | | |
|---|---|---|---|---|---|
| cagcacgagg | aactccttct | gatcacctgg | ccagctgagg | tcagagtggg | agaggcagtg | 60 |
| gttccattga | aggagtactc | ctaactgtca | gaagcctggg | cggtcaggat | ggggtgctgt | 120 |
| cgcttgggct | gcgggggtg | ttcagttgcc | cacagtgtat | ctcagggtct | caccaaccat | 180 |
| ccaagcatgg | taggctgtgg | ctggcaccca | gggttgtgtg | gctggggagg | tggtctccac | 240 |
| agttccctcc | ctgccctccc | agggcccca | tccatgcagg | taaccatcga | ggatgtgcag | 300 |
| gcacagacag | gcggaacggc | ccaattcgag | gctatcattg | agggcgaccc | acagccctcg | 360 |
| gtgacctggt | acaaggacag | cgtccagctg | gtggacagca | cccggcttag | ccagcagcaa | 420 |
| gaaggcacca | catactccct | ggtgctgagg | catgtggcct | cgaaggatgc | cggcgtttac | 480 |
| acctgcctgg | cccaaaacac | tggtggccag | gtgctctgca | aggcagagct | gctggtgctt | 540 |
| ggggggaca | atgagccgga | ctcagagaag | caaagccacc | ggaggaagct | gcactccttc | 600 |
| tatgaggtca | aggaggagat | tggaagggc | gtgtttggct | tcgtaaaaag | agtgcagcac | 660 |
| aaaggaaaca | agatcttgtg | cgctgccaag | ttcatccccc | tacggagcag | aactcgggcc | 720 |
| caggcataca | gggagcgaga | catcctggcc | gcgctgagcc | accgctggt | cacgggctg | 780 |
| ctggaccagt | ttgagacccg | caagaccctc | atcctcatcc | tggagctgtg | ctcatccgag | 840 |
| gagctgctgg | accgcctgta | caggaagggc | gtggtgacgg | aggccgaggt | caaggtctac | 900 |
| atccagcagc | tggtggaggg | gctgcactac | ctgcacagcc | atggcgttct | ccacctggac | 960 |
| ataaagccct | ctaacatcct | gatggtgcat | cctgcccggg | aagacattaa | aatctgcgac | 1020 |
| tttggctttg | cccagaacat | caccccagca | gagctgcagt | tcagccagta | cggctccct | 1080 |
| gagttcgtct | cccccgagat | catccagcag | aaccctgtga | gcgaagcctc | cgacatttgg | 1140 |
| gccatgggtg | tcatctccta | cctcagcctg | acctgctcat | ccctttgc | cggcgagagt | 1200 |
| gaccgtgcca | ccctcctgaa | cgtcctggag | gggcgcgtgt | catggagcag | ccccatggct | 1260 |
| gcccacctca | gcgaagacgc | caaagacttc | atcaaggcta | cgctgcagag | agcccctcag | 1320 |
| gcccggccta | gtgcggccca | gtgcctctcc | caccccctggt | tcctgaaatc | catgcctgcg | 1380 |
| gaggaggccc | acttcatcaa | caccaagcag | ctcaagttcc | tcctggcccg | aagtcgctgg | 1440 |
| cagcgttccc | tgatgagcta | caagtccatc | ctggtgatgc | gctccatccc | tgagctgctg | 1500 |
| cggggcccac | ccgacagccc | ctccctcggc | gtagcccggc | acctctgcag | ggacactggt | 1560 |
| ggctcctcca | gttcctcctc | ctcctctgac | aacgagctcg | cccatttgc | ccgggctaag | 1620 |
| tcactgccac | cctccccggt | gacacactca | ccactgctgc | accccgggg | cttcctgcgg | 1680 |
| ccctcggcca | gctgcctga | ggaagccgag | gccagtgagc | gctccaccga | ggccccagct | 1740 |
| ccgcctgcat | ctcccgaggg | tgccgggcca | ccggccgccc | agggctgcgt | gccccggcac | 1800 |
| agcgtcatcc | gcagcctgtt | ctaccaccag | gcgggtgaga | gccctgagca | ggggccctg | 1860 |
| gccccgggga | gcaggcggca | ccggccggg | cggcggcacc | tgctgaaggg | cggctacatt | 1920 |
| gcgggggcgc | tgccaggcct | gcgcgagcca | ctgatgagc | accgcgtgct | ggaggaggag | 1980 |
| gccgccaggg | aggagcaggc | caccctcctg | gccaaagccc | cctcattcga | gactgccctc | 2040 |

```
cggctgcctg cctctggcac ccacttggcc cctggccaca gccactccct ggaacatgac    2100
tctccgagca cccccccgccc ctcctcggag gcctgcggtg aggcacagcg actgccttca    2160
gccccctccg ggggggcccc tatcaggaac atggggcacc ctcagggctc caagcagctt    2220
ccatccactg gtggccaccc aggcactgct cagccagaga ggccatcccc ggacagccct    2280
tgggggcagc cagcccctt ctgccacccc aagcagggtt ctgcccccca ggagggctgc    2340 agccccacc cagcagttgc cccatgccct cctggctcct tccctccagg atcttgcaaa    2400 gaggcccct tagtaccctc aagccccttc ttgggacagc cccaggcacc ccctgcccct    2460
gccaaagcaa gccccccatt ggactctaag atggggcctg gagacatctc tcttcctggg    2520
aggccaaaac ccggcccctg cagttcccca gggtcagcct cccaggcgag ctcttcccaa    2580
gtgagctccc tcagggtggg ctcctcccag gtgggcacag agcctggccc tccctggat    2640 gcggagggct ggacccagga ggctgaggat ctgtccgact ccacacccac cttgcagcgg    2700
cctcaggaac aggtgaccat cgcaagttc tccctgggtg gtcgcggggg ctacgcaggc    2760
gtggctggct atggcacctt tgcctttggt ggagatgcag gggcatgct ggggcagggg    2820 cccatgtggg ccaggatagc ctgggctgtg tcccagtcgg aggaggagga gcaggaggag    2880
gccagggctg agtcccagtc ggaggagcag caggaggcca gggctgagag cccactgccc    2940
caggtcagtg caaggcctgt gcctgaggtc ggcagggctc ccaccaggag ctctccagag    3000 cccacccat gggaggacat cggcaggtc tccctggtgc agatccggga cctgtcaggt    3060
gatgcggagg cggccgacac aatatccctg gacatttccg aggtggaccc cgcctacctc    3120
aacctctcag acctgtacga tatcaagtac ctcccattcg agtttatgat cttcaggaaa    3180
gtccccaagt ccgctcagcc agagccgccc tcccccatgg ctgaggagga gctggccgag    3240
ttcccggagc ccacgtggcc ctggccaggt gaactgggcc cccacgcagg cctggagatc    3300
acagaggagt cagaggatgt ggacgcgctg ctggcagagg ctgccgtggg caggaagcgc    3360
aagtggtcct cgccgtcacg cagcctcttc cacttccctg ggaggcacct gccgctggat    3420
gagcctgcag agctggggct gcgtgagaga gtgaaggcct ccgtggagca catctcccgg    3480
atcctgaagg gcaggccgga aggtctggag aaggaggggc ccccccaggaa gaagccaggc    3540 cttgcttcct tccggctctc aggtctgaag agctgggacc gagcgccgac attcctaagg    3600
gagctctcag atgagactgt ggtcctgggc cagtcagtga cactggcctg ccaggtgtca    3660
gcccagccag ctgcccaggc cacctggagc aaagacggag cccccctgga gagcagcagc    3720
cgtgtcctca tctctgccac cctcaagaac ttccagcttc tgaccatcct ggtggtggtg    3780
gctgaggacc tgggtgtgta cacctgcagc gtgagcaatg cgctggggac agtgaccacc    3840 acggcgtcc tccggaaggc agagcgcccc tcatcttcgc catgccggga tatcggggag    3900
gtgtacgcgg atgggtgct gctggtctgg aagcccgtgg aatcctacgg ccctgtgacc    3960
tacattgtgc agtgcagcct agaaggcggc agctggacca cactggcctc cgacatcttt    4020
gactgctgct acctgaccag caagctctcc cggggtggca cctacaccct ccgcacggca    4080
tgtgtcagca aggcaggaat gggtccctac agcagcccct cggagcaagt cctcctggga    4140
gggcccagcc acctggcctc tgaggaggag agccaggggc ggtcagccca acccctgccc    4200
agcacaaaga ccttcgcatt ccagacacag atccagaggg gccgcttcag cgtggtgcgg    4260
caatgctggg agaaggccag cgggcgggcg ctggccgcca agatcatccc ctaccacccc    4320
aaggacaaga cagcagtgct gcgcgaatac gaggccctca agggcctgcg ccacccgcac    4380
```

-continued

```
ctggcccagc tgcacgcagc ctacctcagc ccccggcacc tggtgctcat cttggagctg    4440
tgctctgggc ccgagctgct cccctgcctg gccgagaggg cctcctactc agaatctgag    4500
gtgaaggact acctgtggca gatgttgagt gccacccagt acctgcacaa ccagcacatc    4560
ctgcacctgg acctgaggtc cgagaacatg atcatcaccg aatacaacct gctcaaggtc    4620
gtggacctgg gcaatgcaca gagcctcagc caggagaagg tgctgccctc agacaagttc    4680
aaggactacc tagagaccat ggctccagag ctcctggagg ccagggggc tgttccacag     4740 acagacatct gggccatcgg tgtgacagcc ttcatcatgc tgagcgccga gtacccggtg    4800
agcagcgagg gtgcacgcga cctgcagaga ggactgcgca aggggctggt ccggctgagc    4860
cgctgctacg cggggctgtc cggggcgcc gtggccttcc tgcgcagcac tctgtgcgcc     4920
cagccctggg gccggccctg cgcgtccagc tgcctgcagt gcccgtggct aacagaggag    4980
ggcccggcct gttcgcggcc cgcgcccgtg accttcccta ccgcgcggct gcgcgtcttc    5040
gtgcgcaatc gcgagaagag acgcgcgctg ctgtacaaga ggcacaacct ggcccaggtg    5100
cgctgagggt cgccccggcc acaccttggg tctccccgct gggggtcgct gcagacgcgc    5160
caataaaaac gcacagccgg gcgagaaaaa aaaaaaaaaa aaaaaaa                  5207
```

<210> SEQ ID NO 2
<211> LENGTH: 1665
<212> TYPE: PRT
<213> ORGANISM: Human

<400> SEQUENCE: 2

```
Met Gly Cys Cys Arg Leu Gly Cys Gly Gly Cys Ser Val Ala His Ser
 1               5                  10                  15

Val Ser Gln Gly Leu Thr Asn His Pro Ser Met Val Gly Cys Gly Trp
            20                  25                  30

His Pro Gly Leu Cys Gly Trp Gly Gly Leu His Ser Ser Leu Pro
        35                  40                  45

Ala Leu Pro Gly Pro Pro Ser Met Gln Val Thr Ile Glu Asp Val Gln
    50                  55                  60

Ala Gln Thr Gly Gly Thr Ala Gln Phe Glu Ala Ile Ile Glu Gly Asp
65                  70                  75                  80

Pro Gln Pro Ser Val Thr Trp Tyr Lys Asp Ser Val Gln Leu Val Asp
                85                  90                  95

Ser Thr Arg Leu Ser Gln Gln Gln Glu Gly Thr Thr Tyr Ser Leu Val
            100                 105                 110

Leu Arg His Val Ala Ser Lys Asp Ala Gly Val Tyr Thr Cys Leu Ala
        115                 120                 125

Gln Asn Thr Gly Gly Gln Val Leu Cys Lys Ala Glu Leu Leu Val Leu
    130                 135                 140

Gly Gly Asp Asn Glu Pro Asp Ser Glu Lys Gln Ser His Arg Arg Lys
145                 150                 155                 160

Leu His Ser Phe Tyr Glu Val Lys Glu Ile Gly Arg Gly Val Phe
                165                 170                 175

Gly Phe Val Lys Arg Val Gln His Lys Gly Asn Lys Ile Leu Cys Ala
            180                 185                 190

Ala Lys Phe Ile Pro Leu Arg Ser Arg Thr Arg Ala Gln Ala Tyr Arg
        195                 200                 205

Glu Arg Asp Ile Leu Ala Ala Leu Ser His Pro Leu Val Thr Gly Leu
    210                 215                 220

Leu Asp Gln Phe Glu Thr Arg Lys Thr Leu Ile Leu Ile Leu Glu Leu
```

-continued

```
                225                 230                 235                 240
        Cys Ser Ser Glu Glu Leu Leu Asp Arg Leu Tyr Arg Lys Gly Val Val
                            245                 250                 255

Thr Glu Ala Glu Val Lys Val Tyr Ile Gln Gln Leu Val Glu Gly Leu
                            260                 265                 270

His Tyr Leu His Ser His Gly Val Leu His Leu Asp Ile Lys Pro Ser
                            275                 280                 285

Asn Ile Leu Met Val His Pro Ala Arg Glu Asp Ile Lys Ile Cys Asp
                            290                 295                 300

Phe Gly Phe Ala Gln Asn Ile Thr Pro Ala Glu Leu Gln Phe Ser Gln
        305                 310                 315                 320

Tyr Gly Ser Pro Glu Phe Val Ser Pro Glu Ile Ile Gln Gln Asn Pro
                            325                 330                 335

Val Ser Glu Ala Ser Asp Ile Trp Ala Met Gly Val Ile Ser Tyr Leu
                            340                 345                 350

Ser Leu Thr Cys Ser Ser Pro Phe Ala Gly Glu Ser Asp Arg Ala Thr
                            355                 360                 365

Leu Leu Asn Val Leu Glu Gly Arg Val Ser Trp Ser Ser Pro Met Ala
        370                 375                 380

Ala His Leu Ser Glu Asp Ala Lys Asp Phe Ile Lys Ala Thr Leu Gln
        385                 390                 395                 400

Arg Ala Pro Gln Ala Arg Pro Ser Ala Ala Gln Cys Leu Ser His Pro
                            405                 410                 415

Trp Phe Leu Lys Ser Met Pro Ala Glu Glu Ala His Phe Ile Asn Thr
                            420                 425                 430

Lys Gln Leu Lys Phe Leu Leu Ala Arg Ser Arg Trp Gln Arg Ser Leu
                            435                 440                 445

Met Ser Tyr Lys Ser Ile Leu Val Met Arg Ser Ile Pro Glu Leu Leu
        450                 455                 460

Arg Gly Pro Pro Asp Ser Pro Ser Leu Gly Val Ala Arg His Leu Cys
        465                 470                 475                 480

Arg Asp Thr Gly Gly Ser Ser Ser Ser Ser Ser Ser Asp Asn Glu
                            485                 490                 495

Leu Ala Pro Phe Ala Arg Ala Lys Ser Leu Pro Pro Ser Pro Val Thr
                            500                 505                 510

His Ser Pro Leu Leu His Pro Arg Gly Phe Leu Arg Pro Ser Ala Ser
                            515                 520                 525

Leu Pro Glu Glu Ala Glu Ala Ser Glu Arg Ser Thr Glu Ala Pro Ala
                            530                 535                 540

Pro Pro Ala Ser Pro Glu Gly Ala Gly Pro Pro Ala Ala Gln Gly Cys
        545                 550                 555                 560

Val Pro Arg His Ser Val Ile Arg Ser Leu Phe Tyr His Gln Ala Gly
                            565                 570                 575

Glu Ser Pro Glu His Gly Ala Leu Ala Pro Gly Ser Arg Arg His Pro
                            580                 585                 590

Ala Arg Arg His Leu Leu Lys Gly Gly Tyr Ile Ala Gly Ala Leu
                            595                 600                 605

Pro Gly Leu Arg Glu Pro Leu Met Glu His Arg Val Leu Glu Glu Glu
                            610                 615                 620

Ala Ala Arg Glu Glu Gln Ala Thr Leu Leu Ala Lys Ala Pro Ser Phe
        625                 630                 635                 640

Glu Thr Ala Leu Arg Leu Pro Ala Ser Gly Thr His Leu Ala Pro Gly
                            645                 650                 655
```

```
His Ser His Ser Leu Glu His Asp Ser Pro Ser Thr Pro Arg Pro Ser
            660                 665                 670

Ser Glu Ala Cys Gly Glu Ala Gln Arg Leu Pro Ser Ala Pro Ser Gly
        675                 680                 685

Gly Ala Pro Ile Arg Asp Met Gly His Pro Gln Gly Ser Lys Gln Leu
    690                 695                 700

Pro Ser Thr Gly Gly His Pro Gly Thr Ala Gln Pro Glu Arg Pro Ser
705                 710                 715                 720

Pro Asp Ser Pro Trp Gly Gln Pro Ala Pro Phe Cys His Pro Lys Gln
                725                 730                 735

Gly Ser Ala Pro Gln Glu Gly Cys Ser Pro His Pro Ala Val Ala Pro
            740                 745                 750

Cys Pro Pro Gly Ser Phe Pro Gly Ser Cys Lys Glu Ala Pro Leu
        755                 760                 765

Val Pro Ser Ser Pro Phe Leu Gly Gln Pro Gln Ala Pro Pro Ala Pro
    770                 775                 780

Ala Lys Ala Ser Pro Pro Leu Asp Ser Lys Met Gly Pro Gly Asp Ile
785                 790                 795                 800

Ser Leu Pro Gly Arg Pro Lys Pro Gly Pro Cys Ser Ser Pro Gly Ser
                805                 810                 815

Ala Ser Gln Ala Ser Ser Ser Gln Val Ser Ser Leu Arg Val Gly Ser
            820                 825                 830

Ser Gln Val Gly Thr Glu Pro Gly Pro Ser Leu Asp Ala Glu Gly Trp
        835                 840                 845

Thr Gln Glu Ala Glu Asp Leu Ser Asp Ser Thr Pro Thr Leu Gln Arg
    850                 855                 860

Pro Gln Glu Gln Val Thr Met Arg Lys Phe Ser Leu Gly Gly Arg Gly
865                 870                 875                 880

Gly Tyr Ala Gly Val Ala Gly Tyr Gly Thr Phe Ala Phe Gly Gly Asp
                885                 890                 895

Ala Gly Gly Met Leu Gly Gln Gly Pro Met Trp Ala Arg Ile Ala Trp
            900                 905                 910

Ala Val Ser Gln Ser Glu Glu Glu Gln Glu Glu Ala Arg Ala Glu
        915                 920                 925

Ser Gln Ser Glu Glu Gln Gln Glu Ala Arg Ala Glu Ser Pro Leu Pro
930                 935                 940

Gln Val Ser Ala Arg Pro Val Pro Glu Val Gly Arg Ala Pro Thr Arg
945                 950                 955                 960

Ser Ser Pro Glu Pro Thr Pro Trp Glu Asp Ile Gly Gln Val Ser Leu
                965                 970                 975

Val Gln Ile Arg Asp Leu Ser Gly Asp Ala Glu Ala Ala Asp Thr Ile
            980                 985                 990

Ser Leu Asp Ile Ser Glu Val Asp Pro Ala Tyr Leu Asn Leu Ser Asp
        995                 1000                1005

Leu Tyr Asp Ile Lys Tyr Leu Pro Phe Glu Phe Met Ile Phe Arg Lys
    1010                1015                1020

Val Pro Lys Ser Ala Gln Pro Glu Pro Pro Ser Pro Met Ala Glu Glu
1025                1030                1035                1040

Glu Leu Ala Glu Phe Pro Gly Pro Thr Trp Pro Trp Pro Gly Glu Leu
                1045                1050                1055

Gly Pro His Ala Gly Leu Glu Ile Thr Glu Glu Ser Glu Asp Val Asp
            1060                1065                1070
```

-continued

```
Ala Leu Leu Ala Glu Ala Ala Val Gly Arg Lys Arg Lys Trp Ser Ser
        1075                1080                1085
Pro Ser Arg Ser Leu Phe His Phe Pro Gly Arg His Leu Pro Leu Asp
        1090                1095                1100
Glu Pro Ala Glu Leu Gly Leu Arg Glu Arg Val Lys Ala Ser Val Glu
1105                1110                1115                1120
His Ile Ser Arg Ile Leu Lys Gly Arg Pro Glu Gly Leu Glu Lys Glu
                1125                1130                1135
Gly Pro Pro Arg Lys Lys Pro Gly Leu Ala Ser Phe Arg Leu Ser Gly
                1140                1145                1150
Leu Lys Ser Trp Asp Arg Ala Pro Thr Phe Leu Arg Glu Leu Ser Asp
                1155                1160                1165
Glu Thr Val Val Leu Gly Gln Ser Val Thr Leu Ala Cys Gln Val Ser
        1170                1175                1180
Ala Gln Pro Ala Ala Gln Ala Thr Trp Ser Lys Asp Gly Ala Pro Leu
1185                1190                1195                1200
Glu Ser Ser Ser Arg Val Leu Ile Ser Ala Thr Leu Lys Asn Phe Gln
                1205                1210                1215
Leu Leu Thr Ile Leu Val Val Ala Glu Asp Leu Gly Val Tyr Thr
                1220                1225                1230
Cys Ser Val Ser Asn Ala Leu Gly Thr Val Thr Thr Gly Val Leu
        1235                1240                1245
Arg Lys Ala Glu Arg Pro Ser Ser Ser Pro Cys Pro Asp Ile Gly Glu
        1250                1255                1260
Val Tyr Ala Asp Gly Val Leu Leu Val Trp Lys Pro Val Glu Ser Tyr
1265                1270                1275                1280
Gly Pro Val Thr Tyr Ile Val Gln Cys Ser Leu Glu Gly Gly Ser Trp
                1285                1290                1295
Thr Thr Leu Ala Ser Asp Ile Phe Asp Cys Cys Tyr Leu Thr Ser Lys
                1300                1305                1310
Leu Ser Arg Gly Gly Thr Tyr Thr Phe Arg Thr Ala Cys Val Ser Lys
        1315                1320                1325
Ala Gly Met Gly Pro Tyr Ser Ser Pro Ser Glu Gln Val Leu Leu Gly
        1330                1335                1340
Gly Pro Ser His Leu Ala Ser Glu Glu Glu Ser Gln Gly Arg Ser Ala
1345                1350                1355                1360
Gln Pro Leu Pro Ser Thr Lys Thr Phe Ala Phe Gln Thr Gln Ile Gln
                1365                1370                1375
Arg Gly Arg Phe Ser Val Val Arg Gln Cys Trp Glu Lys Ala Ser Gly
                1380                1385                1390
Arg Ala Leu Ala Ala Lys Ile Ile Pro Tyr His Pro Lys Asp Lys Thr
                1395                1400                1405
Ala Val Leu Arg Glu Tyr Glu Ala Leu Lys Gly Leu Arg His Pro His
        1410                1415                1420
Leu Ala Gln Leu His Ala Ala Tyr Leu Ser Pro Arg His Leu Val Leu
1425                1430                1435                1440
Ile Leu Glu Leu Cys Ser Gly Pro Glu Leu Leu Pro Cys Leu Ala Glu
                1445                1450                1455
Arg Ala Ser Tyr Ser Glu Ser Glu Val Lys Asp Tyr Leu Trp Gln Met
                1460                1465                1470
Leu Ser Ala Thr Gln Tyr Leu His Asn Gln His Ile Leu His Leu Asp
        1475                1480                1485
Leu Arg Ser Glu Asn Met Ile Ile Thr Glu Tyr Asn Leu Leu Lys Val
```

```
                1490              1495              1500
Val Asp Leu Gly Asn Ala Gln Ser Leu Ser Gln Glu Lys Val Leu Pro
1505              1510              1515              1520

Ser Asp Lys Phe Lys Asp Tyr Leu Glu Thr Met Ala Pro Glu Leu Leu
                1525              1530              1535

Glu Gly Gln Gly Ala Val Pro Gln Thr Asp Ile Trp Ala Ile Gly Val
            1540              1545              1550

Thr Ala Phe Ile Met Leu Ser Ala Glu Tyr Pro Val Ser Ser Glu Gly
            1555              1560              1565

Ala Arg Asp Leu Gln Arg Gly Leu Arg Lys Gly Leu Val Arg Leu Ser
        1570              1575              1580

Arg Cys Tyr Ala Gly Leu Ser Gly Gly Ala Val Ala Phe Leu Arg Ser
1585              1590              1595              1600

Thr Leu Cys Ala Gln Pro Trp Gly Arg Pro Cys Ala Ser Ser Cys Leu
                1605              1610              1615

Gln Cys Pro Trp Leu Thr Glu Glu Gly Pro Ala Cys Ser Arg Pro Ala
            1620              1625              1630

Pro Val Thr Phe Pro Thr Ala Arg Leu Arg Val Phe Val Arg Asn Arg
        1635              1640              1645

Glu Lys Arg Arg Ala Leu Leu Tyr Lys Arg His Asn Leu Ala Gln Val
    1650              1655              1660

Arg
1665

<210> SEQ ID NO 3
<211> LENGTH: 5207
<212> TYPE: DNA
<213> ORGANISM: Human

<400> SEQUENCE: 3
cagcacgagg aactccttct gatcacctgg ccagctgagg tcagagtggg agaggcagtg      60
gttccattga aggagtactc ctaactgtca gaagcctggg cggtcaggat ggggtgctgt     120
cgcttgggct gcgggggggtg ttcagttgcc cacagtgtat ctcagggtct caccaaccat     180
ccaagcatgg taggctgtgg ctggcaccca gggttgtgtg ctggggagg tggtctccac     240 agttccctcc ctgccctccc agggcccca tccatgcagg taaccatcga ggatgtgcag     300
gcacagacag gcggaacggc ccaattcgag gctatcattg agggcgaccc acagccctcg     360
gtgacctggt acaaggacag cgtccagctg gtggacagca cccggcttag ccagcagcaa     420
gaaggcacca catactccct ggtgctgagg catgtggcct cgaaggatgc cggcgtttac     480
acctgcctgg cccaaaacac tggtggccag gtgctctgca aggcagagct gctggtgctt     540 ggggggaca atgagccgga ctcagagaag caaagccacc ggaggaagct gcactccttc     600
tatgaggtca aggaggagat tggaagggggc gtgtttggct tcgtaaaaag agtgcagcac     660
aaaggaaaca gatcttgtg cgctgccaag ttcatccccc tacggagcag aactcgggcc     720
caggcataca gggagcgaga catcctggcc gcgctgagcc acccgctggt cacggggctg     780
ctggaccagt ttgagacccg caagaccctc atcctcatcc tggagctgtg ctcatccgag     840
gagctgctgg accgcctgta caggaagggc gtggtgacgg aggccgaggt caggtctac     900 atccagcagc tggtggaggg gctgcactac ctgcacagcc atggcgttct ccacctggac     960
ataaagccct ctaacatcct gatggtgcat cctgcccggg aagacattaa aatctgcgac    1020
tttggctttg cccagaacat caccccagca gagctgcagt tcagccagta cggctcccct    1080
```

-continued

```
gagttcgtct cccccgagat catccagcag aaccctgtga gcgaagcctc cgacatttgg    1140
gccatgggtg tcatctccta cctcagcctg acctgctcat ccccatttgc cggcgagagt    1200
gaccgtgcca ccctcctgaa cgtcctggag gggcgcgtgt catggagcag ccccatggct    1260
gcccacctca gcgaagacgc caaagacttc atcaaggcta cgctgcagag agcccctcag    1320
gcccggccta gtgcggccca gtgcctctcc caccctggt tcctgaaatc catgcctgcg     1380
gaggaggccc acttcatcaa caccaagcag ctcaagttcc tcctggcccg aagtcgctgg    1440
cagcgttccc tgatgagcta caagtccatc ctggtgatgc gctccatccc tgagctgctg    1500
cggggcccac ccgacagccc ctccctcggc gtagcccggc acctctgcag ggacactggt    1560
ggctcctcca gttcctcctc ctcctctgac aacgagctcg ccccatttgc ccgggctaag    1620
tcactgccac cctccccggt gacacactca ccactgctgc accccggggg cttcctgcgg    1680
ccctcggcca gctgcctga ggaagccgag gccagtgagc gctccaccga ggccccagct    1740
ccgcctgcat ctcccgaggg tgccgggcca ccggccgccc agggctgcgt gccccggcac    1800
agcgtcatcc gcagcctgtt ctaccaccag gcgggtgaga gccctgagca cggggccctg    1860 gcccccgggga gcaggcggca cccggcccgg cggcggcacc tgctgaaggg cggctacatt    1920
gcgggggcgc tgccaggcct gcgcgagcca ctgatggagc accgcgtgct ggaggaggag    1980
gccgccaggg aggagcaggc caccctcctg gccaaagccc cctcattcga gactgccctc    2040
cggctgcctg cctctggcac ccacttggcc cctggccaca gccactccct ggaacatgac    2100
tctccgagca ccccccgccc ctcctcggag gcctgcggtg aggcacagcg actgccttca    2160 gcccctccg ggggggcccc tatcaggac atggggcacc ctcagggctc caagcagctt    2220
ccatccactg gtgccaccc aggcactgct cagccagaga ggccatcccc ggacagccct    2280 tggggcagc cagccccttt ctgccacccc aagcagggtt ctgcccccca ggagggctgc    2340
agcccccacc cagcagttgc cccatgccct cctggctcct tccctccagg atcttgcaaa    2400 gaggcccccct tagtaccctc aagccccttc ttgggacagc cccaggcacc ccctgcccct    2460
gccaaagcaa gccccccatt ggactctaag atggggcctg gagacatctc tcttcctggg    2520
aggccaaaac ccggcccctg cagttcccca gggtcagcct cccaggcgag ctcttcccaa    2580
gtgagctccc tcagggtggg ctcctcccag gtgggcacag agcctggccc ctccctggat    2640
gcggagggct ggaccaggga ggctgaggat ctgtccgact ccacacccac cttgcagcgg    2700
cctcaggaac aggtgaccat gcgcaagttc tccctgggtg gtcgcggggg ctacgcaggc    2760
gtggctggct atggcacctt tgcctttggt ggagatgcag ggggcatgct ggggcagggg    2820
cccatgtggg ccaggatagc ctgggctgtg tcccagtcgg aggaggagga gcaggaggag    2880
gccagggctg agtcccagtc ggaggagcag caggaggcca gggctgagag cccactgccc    2940
caggtcagtg caaggcctgt gcctgaggtc ggcagggctc ccaccaggag ctctccagag    3000 cccacccat gggaggacat cgggcaggtc tccctggtgc agatccggga cctgtcaggt    3060
gatgcggagg cggccgacac aatatccctg gacatttccg aggtggaccc cgcctacctc    3120
aacctctcag acctgtacga tatcaagtac ctcccattcg agtttatgat cttcaggaaa    3180
gtccccaagt ccgctcagcc agagccgccc tcccccatgg ctgaggagga gctggccgag    3240
ttcccggagc ccacgtggcc ctggccaggt gaactgggcc cccacgcagg cctggagatc    3300
acagaggagt cagaggatgt ggacgcgctg ctggcagagg ctgccgtggg caggaagcgc    3360
aagtggtcct cgccgtcacg cagcctcttc cacttccctg ggaggcacct gccgctggat    3420
gagcctgcag agctggggct gcgtgagaga gtgaaggcct ccgtggagca catctcccgg    3480
```

-continued

```
atcctgaagg gcaggccgga aggtctggag aaggaggggc cccccaggaa gaagccaggc      3540
cttgcttcct tccggctctc aggtctgaag agctgggacc gagcgccgac attcctaagg      3600
gagctctcag atgagactgt ggtcctgggc cagtcagtga cactggcctg ccaggtgtca      3660
gcccagccag ctgcccaggc cacctggagc aaagacggag cccccctgga gagcagcagc      3720
cgtgtcctca tctctgccac cctcaagaac ttccagcttc tgaccatcct ggtggtggtg      3780
gctgaggacc tgggtgtgta cacctgcagc gtgagcaatg cgctggggac agtgaccacc      3840
acgggcgtcc tccggaaggc agagcgcccc tcatcttcgc catgcccgga tatcggggag      3900
gtgtacgcgg atggggtgct gctggtctgg aagcccgtgg aatcctacgg ccctgtgacc      3960
tacattgtgc agtgcagcct agaaggcggc agctggacca cactggcctc cgacatcttt      4020
gactgctgct acctgaccag caagctctcc cggggtggca cctacacctt ccgcacggca      4080
tgtgtcagca aggcaggaat gggtccctac agcagcccct cggagcaagt cctcctggga      4140
gggcccagcc acctggcctc tgaggaggag agccaggggc ggtcagccca acccctgccc      4200
agcacaaaga ccttcgcatt ccagacacag atccagaggg gccgcttcag cgtggtgcgg      4260
caatgctggg agaaggccag cgggcgggcg ctggccgcca agatcatccc ctaccacccc      4320
aaggacaaga cagcagtgct gcgcgaatac gaggccctca agggcctgcg ccacccgcac      4380
ctggcccagc tgcacgcagc ctacctcagc ccccggcacc tggtgctcat cttggagctg      4440
tgctctgggc ccgagctgct ccctgcctg gccgagaggg cctcctactc agaatctgag      4500
gtgaaggact acctgtggca gatgttgagt gccacccagt acctgcacaa ccagcacatc      4560
ctgcacctgg acctgaggtc cgagaacatg atcatcaccg aatacaacct gctcaaggtc      4620
gtggacctgg gcaatgcaca gagcctcagc caggagaagg tgctgccctc agacaagttc      4680
aaggactacc tagagaccat ggctccagag ctcctggagg gccagggggc tgttccacag      4740
acagacatct gggccatcgg tgtgacagcc ttcatcatgc tgagcgccga gtacccggtg      4800
agcagcgagg gtgcacgcga cctgcagaga ggactgcgca aggggctggt ccggctgagc      4860
cgctgctacg cggggctgtc cggggcgcc gtggccttcc tgcgcagcac tctgtgcgcc      4920
cagccctggg gccggccctg cgcgtccagc tgcctgcagt gcccgtggct aacagaggag      4980
ggcccggcct gttcgcggcc cgcgcccgtg accttcccta ccgcgcggct gcgcgtcttc      5040
gtgcgcaatc gcgagaagag acgcgcgctg ctgtacaaga ggcacaacct ggcccaggtg      5100
cgctgagggt cgccccggcc acaccttggg tctccccgct gggggtcgct gcagacgcgc      5160
caataaaaac gcacagccgg gcgagaaaaa aaaaaaaaaa aaaaaaa               5207
```

<210> SEQ ID NO 4
<211> LENGTH: 846
<212> TYPE: PRT
<213> ORGANISM: Human

<400> SEQUENCE: 4

```
Pro Arg Phe Glu Ser Ile Met Glu Asp Val Glu Val Gly Ala Gly Glu
 1               5                  10                  15

Thr Ala Arg Phe Ala Val Val Val Glu Gly Lys Pro Leu Pro Asp Ile
                20                  25                  30

Met Trp Tyr Lys Asp Glu Val Leu Leu Thr Glu Ser Ser His Val Ser
            35                  40                  45

Phe Val Tyr Glu Glu Asn Glu Cys Ser Leu Val Val Leu Ser Thr Gly
        50                  55                  60
```

```
Ala Gln Asp Gly Gly Val Tyr Thr Cys Thr Ala Gln Asn Leu Ala Gly
 65                  70                  75                  80

Glu Val Ser Cys Lys Ala Glu Leu Ala Val His Ser Ala Gln Thr Ala
             85                  90                  95

Met Glu Val Glu Gly Val Gly Glu Asp Glu His Arg Gly Arg Arg
                100                 105                 110

Leu Ser Asp Phe Tyr Asp Ile His Gln Glu Ile Gly Arg Gly Ala Phe
             115                 120                 125

Ser Tyr Leu Arg Arg Ile Val Glu Arg Ser Gly Leu Glu Phe Ala
 130                 135                 140

Ala Lys Phe Ile Pro Ser Gln Ala Lys Pro Lys Ala Ser Ala Arg Arg
 145                 150                 155                 160

Glu Ala Arg Leu Leu Ala Arg Leu Gln His Asp Cys Val Leu Tyr Phe
                 165                 170                 175

His Glu Ala Phe Glu Arg Arg Arg Gly Leu Val Ile Val Thr Glu Leu
             180                 185                 190

Cys Thr Glu Glu Leu Leu Glu Arg Ile Ala Arg Lys Pro Thr Val Cys
         195                 200                 205

Glu Ser Glu Ile Arg Ala Tyr Met Arg Gln Val Leu Glu Gly Ile His
     210                 215                 220

Tyr Leu His Gln Ser His Val Leu His Leu Asp Val Lys Pro Glu Asn
 225                 230                 235                 240

Leu Leu Val Trp Asp Gly Ala Ala Gly Glu Gln Gln Val Arg Ile Cys
                 245                 250                 255

Asp Phe Gly Asn Ala Gln Glu Leu Thr Pro Gly Glu Pro Gln Tyr Cys
             260                 265                 270

Gln Tyr Gly Thr Pro Glu Phe Val Ala Pro Glu Ile Val Asn Gln Ser
         275                 280                 285

Pro Val Ser Gly Val Thr Asp Ile Trp Pro Val Gly Val Val Ala Phe
     290                 295                 300

Leu Cys Leu Thr Gly Ile Ser Pro Phe Val Gly Glu Asn Asp Arg Thr
 305                 310                 315                 320

Thr Leu Met Asn Ile Arg Asn Tyr Asn Val Ala Phe Glu Glu Thr Thr
                 325                 330                 335

Phe Leu Ser Leu Ser Arg Glu Ala Arg Gly Phe Leu Ile Lys Val Leu
             340                 345                 350

Val Gln Asp Arg Leu Arg Pro Thr Ala Glu Glu Thr Leu Glu His Pro
         355                 360                 365

Trp Phe Lys Thr Gln Ala Lys Gly Ala Glu Val Ser Thr Asp His Leu
     370                 375                 380

Lys Leu Phe Leu Ser Arg Arg Arg Trp Gln Arg Ser Gln Ile Ser Tyr
 385                 390                 395                 400

Lys Cys His Leu Val Leu Arg Pro Ile Pro Glu Leu Leu Arg Ala Pro
                 405                 410                 415

Pro Glu Arg Val Trp Val Thr Met Pro Arg Arg Pro Pro Ser Gly
             420                 425                 430

Gly Leu Ser Ser Ser Ser Asp Ser Glu Glu Glu Leu Glu Glu Leu
         435                 440                 445

Pro Ser Val Pro Arg Pro Leu Gln Pro Glu Phe Ser Gly Ser Arg Val
     450                 455                 460

Ser Leu Thr Asp Ile Pro Thr Glu Asp Glu Ala Leu Gly Thr Pro Glu
 465                 470                 475                 480

Thr Gly Ala Ala Thr Pro Met Asp Trp Gln Glu Gln Gly Arg Ala Pro
```

-continued

```
                485                 490                 495
Ser Gln Asp Gln Glu Ala Pro Ser Pro Glu Ala Leu Pro Ser Pro Gly
            500                 505                 510
Gln Glu Pro Ala Ala Gly Ala Ser Pro Arg Arg Gly Glu Leu Arg Arg
        515                 520                 525
Gly Ser Ser Ala Glu Ser Ala Leu Pro Arg Ala Gly Pro Arg Glu Leu
    530                 535                 540
Gly Arg Gly Leu His Lys Ala Ala Ser Val Glu Leu Pro Gln Arg Arg
545                 550                 555                 560
Ser Pro Gly Pro Gly Ala Thr Arg Leu Ala Arg Gly Gly Leu Gly Glu
                565                 570                 575
Gly Glu Tyr Ala Gln Arg Leu Gln Ala Leu Arg Gln Arg Leu Leu Arg
            580                 585                 590
Gly Gly Pro Glu Asp Gly Lys Val Ser Gly Leu Arg Gly Pro Leu Leu
        595                 600                 605
Glu Ser Leu Gly Gly Arg Ala Arg Asp Pro Arg Met Ala Arg Ala Ala
    610                 615                 620
Ser Ser Glu Ala Ala Pro His His Gln Pro Pro Leu Glu Asn Arg Gly
625                 630                 635                 640
Leu Gln Lys Ser Ser Ser Phe Ser Gln Gly Glu Ala Glu Pro Arg Gly
                645                 650                 655
Arg His Arg Arg Ala Gly Ala Pro Leu Glu Ile Pro Val Ala Arg Leu
            660                 665                 670
Gly Ala Arg Arg Leu Gln Glu Ser Pro Ser Leu Ser Ala Leu Ser Glu
        675                 680                 685
Ala Gln Pro Ser Ser Pro Ala Arg Pro Ser Ala Pro Lys Pro Ser Thr
    690                 695                 700
Pro Lys Ser Ala Glu Pro Ser Ala Thr Thr Pro Ser Asp Ala Pro Gln
705                 710                 715                 720
Pro Pro Ala Pro Gln Pro Ala Gln Asp Lys Ala Pro Glu Pro Arg Pro
                725                 730                 735
Glu Pro Val Arg Ala Ser Lys Pro Pro Pro Gln Ala Leu Gln
            740                 745                 750
Thr Leu Ala Leu Pro Leu Thr Pro Tyr Ala Gln Ile Ile Gln Ser Leu
        755                 760                 765
Gln Leu Ser Gly His Ala Gln Gly Pro Ser Gln Gly Pro Ala Ala Pro
    770                 775                 780
Pro Ser Glu Pro Lys Pro His Ala Ala Val Phe Ala Arg Val Ala Ser
785                 790                 795                 800
Pro Pro Pro Gly Ala Pro Glu Lys Arg Val Pro Ser Ala Gly Gly Pro
                805                 810                 815
Pro Val Leu Ala Glu Lys Ala Arg Val Pro Thr Val Pro Pro Arg Pro
            820                 825                 830
Gly Ser Ser Leu Ser Ser Ser Ile Glu Asn Leu Glu Ser Glu
        835                 840                 845

<210> SEQ ID NO 5
<211> LENGTH: 279
<212> TYPE: PRT
<213> ORGANISM: Human

<400> SEQUENCE: 5

Ser Pro Ala Lys Glu Val Val Ser Ser Pro Gly Ser Ser Pro Arg Ser
1               5                   10                  15
```

```
Ser Pro Arg Pro Glu Gly Thr Thr Leu Arg Gln Gly Pro Pro Gln Lys
         20                  25                  30

Pro Tyr Thr Phe Leu Glu Glu Lys Ala Arg Gly Arg Phe Gly Val Val
             35                  40                  45

Arg Ala Cys Arg Glu Asn Ala Thr Gly Arg Thr Phe Val Ala Lys Ile
         50                  55                  60

Val Pro Tyr Ala Ala Glu Gly Lys Pro Arg Val Leu Gln Glu Tyr Glu
 65                  70                  75                  80

Val Leu Arg Thr Leu His His Glu Arg Ile Met Ser Leu His Glu Ala
                 85                  90                  95

Tyr Ile Thr Pro Arg Tyr Leu Val Leu Ile Ala Glu Ser Cys Gly Asn
             100                 105                 110

Arg Glu Leu Leu Cys Gly Leu Ser Asp Arg Phe Arg Tyr Ser Glu Asp
         115                 120                 125

Asp Val Ala Thr Tyr Met Val Gln Leu Leu Gln Gly Leu Asp Tyr Leu
         130                 135                 140

His Gly His His Val Leu His Leu Asp Ile Lys Pro Asp Asn Leu Leu
145                 150                 155                 160

Leu Ala Pro Asp Asn Ala Leu Lys Ile Val Asp Phe Gly Ser Ala Gln
                 165                 170                 175

Pro Tyr Asn Pro Gln Ala Leu Arg Pro Leu Gly His Arg Thr Gly Thr
             180                 185                 190

Leu Glu Phe Met Ala Pro Glu Met Val Lys Gly Glu Pro Ile Gly Ser
         195                 200                 205

Ala Thr Asp Ile Trp Gly Ala Gly Val Leu Thr Tyr Ile Met Leu Ser
         210                 215                 220

Gly Arg Ser Pro Phe Tyr Glu Pro Asp Pro Gln Glu Thr Glu Ala Arg
225                 230                 235                 240

Ile Val Gly Gly Arg Phe Asp Ala Phe Gln Leu Tyr Pro Asn Thr Ser
                 245                 250                 255

Gln Ser Ala Thr Leu Phe Leu Arg Lys Val Leu Ser Val His Pro Trp
             260                 265                 270

Ser Arg Pro Ser Ser Cys Leu
             275

<210> SEQ ID NO 6
<211> LENGTH: 549
<212> TYPE: PRT
<213> ORGANISM: Human

<400> SEQUENCE: 6

Leu Arg Glu Pro Gly Trp Ala Ala Thr Gly Leu Arg Lys Gly Val Gln
 1               5                  10                  15

His Ile Phe Arg Val Leu Ser Thr Thr Val Lys Ser Ser Ser Lys Pro
             20                  25                  30

Ser Pro Pro Ser Glu Pro Val Gln Leu Leu Glu His Gly Pro Thr Leu
         35                  40                  45

Glu Glu Ala Pro Ala Met Leu Asp Lys Pro Asp Ile Val Tyr Val Val
     50                  55                  60

Glu Gly Gln Pro Ala Ser Val Thr Val Thr Phe Asn His Val Glu Ala
 65                  70                  75                  80

Gln Val Val Trp Arg Ser Cys Arg Gly Ala Leu Leu Glu Ala Arg Ala
                 85                  90                  95

Gly Val Tyr Glu Leu Ser Gln Pro Asp Asp Gln Tyr Cys Leu Arg
             100                 105                 110
```

```
Ile Cys Arg Val Ser Arg Arg Asp Met Gly Ala Leu Thr Cys Thr Ala
        115                 120                 125
Arg Asn Arg His Gly Thr Gln Thr Cys Ser Val Thr Leu Glu Leu Ala
    130                 135                 140
Glu Ala Pro Arg Phe Glu Ser Ile Met Glu Asp Val Glu Val Gly Ala
145                 150                 155                 160
Gly Glu Thr Ala Arg Phe Ala Val Val Glu Gly Lys Pro Leu Pro
                165                 170                 175
Asp Ile Met Trp Tyr Lys Asp Glu Val Leu Leu Thr Glu Ser Ser His
            180                 185                 190
Val Ser Phe Val Tyr Glu Glu Asn Glu Cys Ser Leu Val Val Leu Ser
        195                 200                 205
Thr Gly Ala Gln Asp Gly Gly Val Tyr Thr Cys Thr Ala Gln Asn Leu
    210                 215                 220
Ala Gly Glu Val Ser Cys Lys Ala Glu Leu Ala Val His Ser Ala Gln
225                 230                 235                 240
Thr Ala Met Glu Val Glu Gly Val Gly Glu Asp Glu His Arg Gly
                245                 250                 255
Arg Arg Leu Ser Asp Phe Tyr Asp Ile His Gln Glu Ile Gly Arg Gly
            260                 265                 270
Ala Phe Ser Tyr Leu Arg Arg Ile Val Glu Arg Ser Ser Gly Leu Glu
        275                 280                 285
Phe Ala Ala Lys Phe Ile Pro Ser Gln Ala Lys Pro Lys Ala Ser Ala
            290                 295                 300
Arg Arg Glu Ala Arg Leu Leu Ala Arg Leu Gln His Asp Cys Val Leu
305                 310                 315                 320
Tyr Phe His Glu Ala Phe Glu Arg Arg Gly Leu Val Ile Val Thr
                325                 330                 335
Glu Leu Cys Thr Glu Glu Leu Leu Glu Arg Ile Ala Arg Lys Pro Thr
            340                 345                 350
Val Cys Glu Ser Glu Ile Arg Ala Tyr Met Arg Gln Val Leu Glu Gly
        355                 360                 365
Ile His Tyr Leu His Gln Ser His Val Leu His Leu Asp Val Lys Pro
    370                 375                 380
Glu Asn Leu Leu Val Trp Asp Gly Ala Ala Gly Glu Gln Gln Val Arg
385                 390                 395                 400
Ile Cys Asp Phe Gly Asn Ala Gln Glu Leu Thr Pro Gly Glu Pro Gln
                405                 410                 415
Tyr Cys Gln Tyr Gly Thr Pro Glu Phe Val Ala Pro Glu Ile Val Asn
            420                 425                 430
Gln Ser Pro Val Ser Gly Val Thr Asp Ile Trp Pro Val Gly Val Val
        435                 440                 445
Ala Phe Leu Cys Leu Thr Gly Ile Ser Pro Phe Val Gly Glu Asn Asp
            450                 455                 460
Arg Thr Thr Leu Met Asn Ile Arg Asn Tyr Asn Val Ala Phe Glu Glu
465                 470                 475                 480
Thr Thr Phe Leu Ser Leu Ser Arg Glu Ala Arg Gly Phe Leu Ile Lys
                485                 490                 495
Val Leu Val Gln Asp Arg Leu Arg Pro Thr Ala Glu Glu Thr Leu Glu
            500                 505                 510
His Pro Trp Phe Lys Thr Gln Ala Lys Gly Ala Glu Val Ser Thr Asp
        515                 520                 525
```

```
His Leu Lys Leu Phe Leu Ser Arg Arg Trp Gln Arg Ser Gln Ile
    530                 535                 540

Ser Tyr Lys Cys His
545

<210> SEQ ID NO 7
<211> LENGTH: 250
<212> TYPE: PRT
<213> ORGANISM: Human

<400> SEQUENCE: 7

Tyr Thr Phe Leu Glu Glu Lys Ala Arg Gly Arg Phe Gly Val Val Arg
  1               5                  10                  15

Ala Cys Arg Glu Asn Ala Thr Gly Arg Thr Phe Val Ala Lys Ile Val
             20                  25                  30

Pro Tyr Ala Ala Glu Gly Lys Pro Arg Val Leu Gln Glu Tyr Glu Val
         35                  40                  45

Leu Arg Thr Leu His His Glu Arg Ile Met Ser Leu His Glu Ala Tyr
     50                  55                  60

Ile Thr Pro Arg Tyr Leu Val Leu Ile Ala Glu Ser Cys Gly Asn Arg
 65                  70                  75                  80

Glu Leu Leu Cys Gly Leu Ser Asp Arg Phe Arg Tyr Ser Glu Asp Asp
                 85                  90                  95

Val Ala Thr Tyr Met Val Gln Leu Leu Gln Gly Leu Asp Tyr Leu His
            100                 105                 110

Gly His His Val Leu His Leu Asp Ile Lys Pro Asp Asn Leu Leu Leu
        115                 120                 125

Ala Pro Asp Asn Ala Leu Lys Ile Val Asp Phe Gly Ser Ala Gln Pro
    130                 135                 140

Tyr Asn Pro Gln Ala Leu Arg Pro Leu Gly His Arg Thr Gly Thr Leu
145                 150                 155                 160

Glu Phe Met Ala Pro Glu Met Val Lys Gly Glu Pro Ile Gly Ser Ala
                165                 170                 175

Thr Asp Ile Trp Gly Ala Gly Val Leu Thr Tyr Ile Met Leu Ser Gly
            180                 185                 190

Arg Ser Pro Phe Tyr Glu Pro Asp Pro Gln Glu Thr Glu Ala Arg Ile
        195                 200                 205

Val Gly Gly Arg Phe Asp Ala Phe Gln Leu Tyr Pro Asn Thr Ser Gln
    210                 215                 220

Ser Ala Thr Leu Phe Leu Arg Lys Val Leu Ser Val His Pro Trp Ser
225                 230                 235                 240

Arg Pro Ser Ser Cys Leu Ser Val Cys His
                245                 250

<210> SEQ ID NO 8
<211> LENGTH: 245
<212> TYPE: PRT
<213> ORGANISM: Human

<400> SEQUENCE: 8

Pro Arg Lys Asp Lys Gly Leu Ser Pro Pro Asn Leu Ser Ala Ser Val
  1               5                  10                  15

Gln Glu Glu Leu Gly His Gln Tyr Val Arg Ser Glu Ser Asp Phe Pro
             20                  25                  30

Pro Val Phe His Ile Lys Leu Lys Asp Gln Val Leu Leu Glu Gly Glu
         35                  40                  45
```

-continued

```
Ala Ala Thr Leu Leu Cys Leu Pro Ala Ala Cys Pro Ala Pro His Ile
 50                  55                  60

Ser Trp Met Lys Asp Lys Ser Leu Arg Ser Glu Pro Ser Val Ile
 65                  70                  75                  80

Ile Val Ser Cys Lys Asp Gly Arg Gln Leu Ser Ile Pro Arg Ala
                 85                  90                  95

Gly Lys Arg His Ala Gly Leu Tyr Glu Cys Ser Ala Thr Asn Val Leu
                100                 105                 110

Gly Ser Ile Thr Ser Ser Cys Thr Val Ala Val Ala Arg Val Pro Gly
            115                 120                 125

Lys Leu Ala Pro Pro Glu Val Thr Gln Thr Tyr Gln Asp Thr Ala Leu
        130                 135                 140

Val Leu Trp Lys Pro Gly Asp Ser Arg Ala Pro Cys Thr Tyr Thr Leu
145                 150                 155                 160

Glu Arg Arg Val Asp Gly Glu Ser Val Trp His Pro Val Ser Ser Gly
                165                 170                 175

Ile Pro Asp Cys Tyr Tyr Asn Val Thr His Leu Pro Val Gly Val Thr
                180                 185                 190

Val Arg Phe Arg Val Ala Cys Ala Asn Arg Ala Gly Gln Gly Pro Phe
            195                 200                 205

Ser Asn Ser Ser Glu Lys Val Phe Val Arg Gly Thr Gln Asp Ser Ser
        210                 215                 220

Ala Val Pro Ser Ala Ala His Gln Glu Ala Pro Val Thr Ser Arg Pro
225                 230                 235                 240

Ala Arg Ala Arg Pro
                245

<210> SEQ ID NO 9
<211> LENGTH: 111
<212> TYPE: PRT
<213> ORGANISM: Human

<400> SEQUENCE: 9

Leu Glu Asp Val Glu Val Leu Glu Gly Arg Ala Ala Arg Phe Asp Cys
  1               5                  10                  15

Lys Ile Ser Gly Thr Pro Pro Val Val Thr Trp Thr His Phe Gly
                 20                  25                  30

Cys Pro Met Glu Glu Ser Glu Asn Leu Arg Leu Arg Gln Asp Gly Gly
             35                  40                  45

Leu His Ser Leu His Ile Ala His Val Gly Ser Glu Asp Glu Gly Leu
         50                  55                  60

Tyr Ala Val Ser Ala Val Asn Thr His Gly Gln Ala His Cys Ser Ala
 65                  70                  75                  80

Gln Leu Tyr Val Glu Glu Pro Arg Thr Ala Ala Ser Gly Pro Ser Ser
                 85                  90                  95

Lys Leu Glu Lys Met Pro Ser Ile Pro Glu Glu Pro Glu Gln Gly
            100                 105                 110

<210> SEQ ID NO 10
<211> LENGTH: 198
<212> TYPE: PRT
<213> ORGANISM: Human

<400> SEQUENCE: 10

Pro Asp Phe Leu Arg Pro Leu Gln Asp Leu Glu Val Gly Leu Ala Lys
  1               5                  10                  15
```

Glu Ala Met Leu Glu Cys Gln Val Thr Gly Leu Pro Tyr Pro Thr Ile
            20                  25                  30

Ser Trp Phe His Asn Gly His Arg Ile Gln Ser Ser Asp Arg Arg
            35                  40                  45

Met Thr Gln Tyr Arg Asp Val His Arg Leu Val Phe Pro Ala Val Gly
            50                  55                  60

Pro Gln His Ala Gly Val Tyr Lys Ser Val Ile Ala Asn Lys Leu Gly
65                  70                  75                  80

Lys Ala Ala Cys Tyr Ala His Leu Tyr Val Thr Asp Val Val Pro Gly
                85                  90                  95

Pro Pro Asp Gly Ala Pro Gln Val Val Ala Val Thr Gly Arg Met Val
                100                 105                 110

Thr Leu Thr Trp Asn Pro Pro Arg Ser Leu Asp Met Ala Ile Asp Pro
            115                 120                 125

Asp Ser Leu Thr Tyr Thr Val Gln His Gln Val Leu Gly Ser Asp Gln
130                 135                 140

Trp Thr Ala Leu Val Thr Gly Leu Arg Glu Pro Gly Trp Ala Ala Thr
145                 150                 155                 160

Gly Leu Arg Lys Gly Val Gln His Ile Phe Arg Val Leu Ser Thr Thr
                165                 170                 175

Val Lys Ser Ser Lys Pro Ser Pro Ser Glu Pro Val Gln Leu
            180                 185                 190

Leu Glu His Gly Pro Thr
            195

<210> SEQ ID NO 11
<211> LENGTH: 101
<212> TYPE: PRT
<213> ORGANISM: Human

<400> SEQUENCE: 11

Ala Pro Leu Phe Thr Arg Leu Leu Glu Asp Val Glu Val Leu Glu Gly
1               5                   10                  15

Arg Ala Ala Arg Phe Asp Cys Lys Ile Ser Gly Thr Pro Pro Pro Val
            20                  25                  30

Val Thr Trp Thr His Phe Gly Cys Pro Met Glu Glu Ser Glu Asn Leu
            35                  40                  45

Arg Leu Arg Gln Asp Gly Gly Leu His Ser Leu His Ile Ala His Val
        50                  55                  60

Gly Ser Glu Asp Glu Gly Leu Tyr Ala Val Ser Ala Val Asn Thr His
65                  70                  75                  80

Gly Gln Ala His Cys Ser Ala Gln Leu Tyr Val Glu Glu Pro Arg Thr
                85                  90                  95

Ala Ala Ser Gly Pro
            100

<210> SEQ ID NO 12
<211> LENGTH: 195
<212> TYPE: PRT
<213> ORGANISM: Human

<400> SEQUENCE: 12

Arg Gly Thr Gln Asp Ser Ser Ala Val Pro Ser Ala Ala His Gln Glu
1               5                   10                  15

Ala Pro Val Thr Ser Arg Pro Ala Arg Ala Arg Pro Pro Asp Ser Pro
            20                  25                  30

-continued

```
Thr Ser Leu Ala Pro Leu Ala Pro Ala Pro Thr Pro Pro Ser
        35              40                  45

Val Thr Val Ser Pro Ser Ser Pro Pro Thr Pro Ser Gln Ala Leu
 50              55                  60

Ser Ser Leu Lys Ala Val Gly Pro Pro Gln Thr Pro Arg Arg
 65              70                  75              80

His Arg Gly Leu Gln Ala Ala Arg Pro Ala Glu Pro Thr Leu Pro Ser
                85                  90                  95

Thr His Val Thr Pro Ser Glu Pro Lys Pro Phe Val Leu Asp Thr Gly
                100                 105                 110

Thr Pro Ile Pro Ala Ser Thr Pro Gln Gly Val Lys Pro Val Ser Ser
                115                 120                 125

Ser Thr Pro Val Tyr Val Val Thr Ser Phe Val Ser Ala Pro Pro Ala
        130                 135                 140

Pro Glu Pro Pro Ala Pro Glu Pro Pro Glu Pro Thr Lys Val Thr
145                 150                 155                 160

Val Gln Ser Leu Ser Pro Ala Lys Glu Val Val Ser Ser Pro Gly Ser
                165                 170                 175

Ser Pro Arg Ser Ser Pro Arg Pro Glu Gly Thr Thr Leu Arg Gln Gly
                180                 185                 190

Pro Pro Gln
        195

<210> SEQ ID NO 13
<211> LENGTH: 90
<212> TYPE: PRT
<213> ORGANISM: Human

<400> SEQUENCE: 13

Pro Asp Phe Leu Arg Pro Leu Gln Asp Leu Glu Val Gly Leu Ala Lys
 1               5                  10                  15

Glu Ala Met Leu Glu Cys Gln Val Thr Gly Leu Pro Tyr Pro Thr Ile
                20                  25                  30

Ser Trp Phe His Asn Gly His Arg Ile Gln Ser Ser Asp Asp Arg Arg
        35                  40                  45

Met Thr Gln Tyr Arg Asp Val His Arg Leu Val Phe Pro Ala Val Gly
 50                  55                  60

Pro Gln His Ala Gly Val Tyr Lys Ser Val Ile Ala Asn Lys Leu Gly
 65                  70                  75                  80

Lys Ala Ala Cys Tyr Ala His Leu Tyr Val
                85                  90

<210> SEQ ID NO 14
<211> LENGTH: 414
<212> TYPE: PRT
<213> ORGANISM: Human

<400> SEQUENCE: 14

Pro Pro Glu Phe Val Ile Pro Leu Ser Glu Val Thr Cys Glu Thr Gly
 1               5                  10                  15

Glu Thr Val Val Leu Arg Cys Arg Val Cys Gly Arg Pro Lys Ala Ser
                20                  25                  30

Ile Thr Trp Lys Gly Pro Glu His Asn Thr Leu Asn Asn Asp Gly His
        35                  40                  45

Tyr Ser Ile Ser Tyr Ser Asp Leu Gly Glu Ala Thr Leu Lys Ile Val
 50                  55                  60
```

```
Gly Val Thr Thr Glu Asp Asp Gly Ile Tyr Thr Cys Ile Ala Val Asn
 65                  70                  75                  80

Asp Met Gly Ser Ala Ser Ser Ala Ser Leu Arg Val Leu Gly Pro
                 85                  90                  95

Gly Met Asp Gly Ile Met Val Thr Trp Lys Asp Asn Phe Asp Ser Phe
                100                 105                 110

Tyr Ser Glu Val Ala Glu Leu Gly Arg Gly Arg Phe Ser Val Val Lys
            115                 120                 125

Lys Cys Asp Gln Lys Gly Thr Lys Arg Ala Val Ala Thr Lys Phe Val
130                 135                 140

Asn Lys Lys Leu Met Lys Arg Asp Gln Val Thr His Glu Leu Gly Ile
145                 150                 155                 160

Leu Gln Ser Leu Gln His Pro Leu Leu Val Gly Leu Leu Asp Thr Phe
                165                 170                 175

Glu Thr Pro Thr Ser Tyr Ile Leu Val Leu Glu Met Ala Asp Gln Gly
            180                 185                 190

Arg Leu Leu Asp Cys Val Val Arg Trp Gly Ser Leu Thr Glu Gly Lys
        195                 200                 205

Ile Arg Ala His Leu Gly Glu Val Leu Glu Ala Val Arg Tyr Leu His
    210                 215                 220

Asn Cys Arg Ile Ala His Leu Asp Leu Lys Pro Glu Asn Ile Leu Val
225                 230                 235                 240

Asp Glu Ser Leu Ala Lys Pro Thr Ile Lys Leu Ala Asp Phe Gly Asp
                245                 250                 255

Ala Val Gln Leu Asn Thr Thr Tyr Tyr Ile His Gln Leu Leu Gly Asn
            260                 265                 270

Pro Glu Phe Ala Ala Pro Glu Ile Ile Leu Gly Asn Pro Val Ser Leu
        275                 280                 285

Thr Ser Asp Thr Trp Ser Val Gly Val Leu Thr Tyr Val Leu Leu Ser
    290                 295                 300

Gly Val Ser Pro Phe Leu Asp Asp Ser Val Glu Glu Thr Cys Leu Asn
305                 310                 315                 320

Ile Cys Arg Leu Asp Phe Ser Phe Pro Asp Asp Tyr Phe Lys Gly Val
                325                 330                 335

Ser Gln Lys Ala Lys Glu Phe Val Cys Phe Leu Leu Gln Glu Asp Pro
            340                 345                 350

Ala Lys Arg Pro Ser Ala Ala Leu Ala Leu Gln Glu Gln Trp Leu Gln
        355                 360                 365

Ala Gly Asn Gly Arg Ser Thr Gly Val Leu Asp Thr Ser Arg Leu Thr
    370                 375                 380

Ser Phe Ile Glu Arg Arg Lys His Gln Asn Asp Val Arg Pro Ile Arg
385                 390                 395                 400

Ser Ile Lys Asn Phe Leu Gln Ser Arg Leu Leu Pro Arg Val
                405                 410

<210> SEQ ID NO 15
<211> LENGTH: 274
<212> TYPE: PRT
<213> ORGANISM: Human

<400> SEQUENCE: 15

Glu Leu Gly Arg Gly Arg Phe Ser Val Val Lys Lys Cys Asp Gln Lys
  1               5                  10                  15

Gly Thr Lys Arg Ala Val Ala Thr Lys Phe Val Asn Lys Lys Leu Met
                 20                  25                  30
```

-continued

```
Lys Arg Asp Gln Val Thr His Glu Leu Gly Ile Leu Gln Ser Leu Gln
            35                  40                  45

His Pro Leu Leu Val Gly Leu Leu Asp Thr Phe Glu Thr Pro Thr Ser
        50                  55                  60

Tyr Ile Leu Val Leu Glu Met Ala Asp Gln Gly Arg Leu Leu Asp Cys
65                  70                  75                  80

Val Val Arg Trp Gly Ser Leu Thr Glu Gly Lys Ile Arg Ala His Leu
                    85                  90                  95

Gly Glu Val Leu Glu Ala Val Arg Tyr Leu His Asn Cys Arg Ile Ala
                100                 105                 110

His Leu Asp Leu Lys Pro Glu Asn Ile Leu Val Asp Glu Ser Leu Ala
            115                 120                 125

Lys Pro Thr Ile Lys Leu Ala Asp Phe Gly Asp Ala Val Gln Leu Asn
        130                 135                 140

Thr Thr Tyr Tyr Ile His Gln Leu Leu Gly Asn Pro Glu Phe Ala Ala
145                 150                 155                 160

Pro Glu Ile Ile Leu Gly Asn Pro Val Ser Leu Thr Ser Asp Thr Trp
                    165                 170                 175

Ser Val Gly Val Leu Thr Tyr Val Leu Leu Ser Gly Val Ser Pro Phe
                180                 185                 190

Leu Asp Asp Ser Val Glu Glu Thr Cys Leu Asn Ile Cys Arg Leu Asp
            195                 200                 205

Phe Ser Phe Pro Asp Asp Tyr Phe Lys Gly Val Ser Gln Lys Ala Lys
        210                 215                 220

Glu Phe Val Cys Phe Leu Leu Gln Glu Asp Pro Ala Lys Arg Pro Ser
225                 230                 235                 240

Ala Ala Leu Ala Leu Gln Glu Gln Trp Leu Gln Ala Gly Asn Gly Arg
                    245                 250                 255

Ser Thr Gly Val Leu Asp Thr Ser Arg Leu Thr Ser Phe Ile Glu Arg
                260                 265                 270

Arg Lys

<210> SEQ ID NO 16
<211> LENGTH: 141
<212> TYPE: PRT
<213> ORGANISM: Human

<400> SEQUENCE: 16

Gly Lys Arg Glu Gly Lys Leu Glu Asn Gly Tyr Arg Lys Ser Arg Glu
1               5                   10                  15

Gly Leu Ser Asn Lys Val Ser Val Lys Leu Leu Asn Pro Asn Tyr Ile
            20                  25                  30

Tyr Asp Val Pro Pro Glu Phe Val Ile Pro Leu Ser Glu Val Thr Cys
        35                  40                  45

Glu Thr Gly Glu Thr Val Val Leu Arg Cys Arg Val Cys Gly Arg Pro
    50                  55                  60

Lys Ala Ser Ile Thr Trp Lys Gly Pro Glu His Asn Thr Leu Asn Asn
65                  70                  75                  80

Asp Gly His Tyr Ser Ile Ser Tyr Ser Asp Leu Gly Glu Ala Thr Leu
                85                  90                  95

Lys Ile Val Gly Val Thr Thr Glu Asp Asp Gly Ile Tyr Thr Cys Ile
            100                 105                 110

Ala Val Asn Asp Met Gly Ser Ala Ser Ser Ala Ser Leu Arg Val
        115                 120                 125
```

```
Leu Gly Pro Gly Met Asp Gly Ile Met Val Thr Trp Lys
        130                 135                 140

<210> SEQ ID NO 17
<211> LENGTH: 196
<212> TYPE: PRT
<213> ORGANISM: Human

<400> SEQUENCE: 17

Gly Gly Ala Pro Ser Gly Gly Ser Gly His Ser Gly Gly Pro Ser Ser
  1               5                  10                  15

Cys Gly Gly Ala Pro Ser Thr Ser Arg Ser Arg Pro Ser Arg Ile Pro
             20                  25                  30

Gln Pro Val Arg His His Pro Val Leu Val Ser Ser Ala Ala Ser
         35                  40                  45

Ser Gln Ala Glu Ala Asp Lys Met Ser Gly Thr Ser Thr Pro Gly Pro
     50                  55                  60

Ser Leu Pro Pro Gly Ala Ala Pro Glu Ala Gly Pro Ser Ala Pro
 65                  70                  75                  80

Ser Arg Arg Pro Pro Gly Ala Asp Ala Glu Gly Ser Glu Arg Glu Ala
                 85                  90                  95

Glu Pro Ile Pro Lys Met Lys Val Leu Glu Ser Pro Arg Lys Gly Ala
                100                 105                 110

Ala Asn Ala Ser Gly Ser Ser Pro Asp Ala Pro Ala Lys Asp Ala Arg
            115                 120                 125

Ala Ser Leu Gly Thr Leu Pro Leu Gly Lys Pro Arg Ala Gly Ala Ala
        130                 135                 140

Ser Pro Leu Asn Ser Pro Leu Ser Ser Ala Val Pro Ser Leu Gly Lys
145                 150                 155                 160

Glu Pro Phe Pro Pro Ser Ser Pro Leu Gln Lys Gly Gly Ser Phe Trp
                165                 170                 175

Ser Ser Ile Pro Ala Ser Pro Ala Ser Arg Pro Gly Ser Phe Thr Phe
            180                 185                 190

Pro Gly Asp Ser
        195

<210> SEQ ID NO 18
<211> LENGTH: 298
<212> TYPE: PRT
<213> ORGANISM: Human

<400> SEQUENCE: 18

Gln Lys Val Ser Asp Phe Tyr Asp Ile Glu Glu Arg Leu Gly Ser Gly
  1               5                  10                  15

Lys Phe Gly Gln Val Phe Arg Leu Val Glu Lys Lys Thr Arg Lys Val
             20                  25                  30

Trp Ala Gly Lys Phe Phe Lys Ala Tyr Ser Ala Lys Glu Lys Glu Asn
         35                  40                  45

Ile Arg Gln Glu Ile Ser Ile Met Asn Cys Leu His His Pro Lys Leu
     50                  55                  60

Val Gln Cys Val Asp Ala Phe Glu Glu Lys Ala Asn Ile Val Met Val
 65                  70                  75                  80

Leu Glu Ile Val Ser Gly Gly Glu Leu Phe Glu Arg Ile Ile Asp Glu
                 85                  90                  95

Asp Phe Glu Leu Thr Glu Arg Glu Cys Ile Lys Tyr Met Arg Gln Ile
                100                 105                 110
```

```
Ser Glu Gly Val Glu Tyr Ile His Lys Gln Gly Ile Val His Leu Asp
    115                 120                 125

Leu Lys Pro Glu Asn Ile Met Cys Val Asn Lys Thr Gly Thr Arg Ile
130                 135                 140

Lys Leu Ile Asp Phe Gly Leu Ala Arg Arg Leu Glu Asn Ala Gly Ser
145                 150                 155                 160

Leu Lys Val Leu Phe Gly Thr Pro Glu Phe Val Ala Pro Glu Val Ile
                165                 170                 175

Asn Tyr Glu Pro Ile Ser Tyr Ala Thr Asp Met Trp Ser Ile Gly Val
            180                 185                 190

Ile Cys Tyr Ile Leu Val Ser Gly Leu Ser Pro Phe Met Gly Asp Asn
        195                 200                 205

Asp Asn Glu Thr Leu Ala Asn Val Thr Ser Ala Thr Trp Asp Phe Asp
    210                 215                 220

Asp Glu Ala Phe Asp Glu Ile Ser Asp Ala Lys Asp Phe Ile Ser
225                 230                 235                 240

Asn Leu Leu Lys Lys Asp Met Lys Asn Arg Leu Asp Cys Thr Gln Cys
                245                 250                 255

Leu Gln His Pro Trp Leu Met Lys Asp Thr Lys Asn Met Glu Ala Lys
            260                 265                 270

Lys Leu Ser Lys Asp Arg Met Lys Lys Tyr Met Ala Arg Arg Lys Trp
        275                 280                 285

Gln Lys Thr Gly Asn Ala Val Arg Ala Ile
    290                 295

<210> SEQ ID NO 19
<211> LENGTH: 508
<212> TYPE: PRT
<213> ORGANISM: Human

<400> SEQUENCE: 19

Gly Thr Glu Ser Asp Ala Thr Val Lys Lys Pro Ala Pro Lys Thr
1               5                   10                  15

Pro Pro Lys Ala Ala Met Pro Pro Gln Ile Ile Gln Phe Pro Glu Asp
                20                  25                  30

Gln Lys Val Arg Ala Gly Glu Ser Val Glu Leu Phe Gly Lys Val Thr
            35                  40                  45

Gly Thr Gln Pro Ile Thr Cys Thr Trp Met Lys Phe Arg Lys Gln Ile
        50                  55                  60

Gln Asp Ser Glu His Ile Lys Val Glu Asn Ser Glu Asn Gly Ser Lys
65                  70                  75                  80

Leu Thr Ile Leu Ala Ala Arg Gln Glu His Cys Gly Cys Tyr Thr Leu
                85                  90                  95

Leu Val Glu Asn Lys Leu Gly Ser Arg Gln Ala Gln Val Asn Leu Thr
                100                 105                 110

Val Val Asp Lys Pro Asp Pro Ala Gly Thr Pro Cys Ala Ser Asp
            115                 120                 125

Ile Arg Ser Ser Ser Leu Thr Leu Ser Trp Tyr Gly Ser Ser Tyr Asp
        130                 135                 140

Gly Gly Ser Ala Val Gln Ser Tyr Ser Ile Glu Ile Trp Asp Ser Ala
145                 150                 155                 160

Asn Lys Thr Trp Lys Glu Leu Ala Thr Cys Arg Ser Thr Ser Phe Asn
                165                 170                 175

Val Gln Asp Leu Leu Pro Asp His Glu Tyr Lys Phe Arg Val Arg Ala
```

-continued

```
                    180                 185                 190
Ile Asn Val Tyr Gly Thr Ser Glu Pro Ser Gln Glu Ser Glu Leu Thr
            195                 200                 205
Thr Val Gly Glu Lys Pro Glu Pro Lys Met Lys Trp Arg Cys Gln
        210                 215                 220
Thr Asp Glu Lys Glu Pro Glu Val Asp Tyr Arg Thr Val Thr Ile
225                 230                 235                 240
Asn Thr Glu Gln Lys Val Ser Asp Phe Tyr Asp Ile Glu Arg Leu
                245                 250                 255
Gly Ser Gly Lys Phe Gly Gln Val Phe Arg Leu Val Glu Lys Thr
            260                 265                 270
Arg Lys Val Trp Ala Gly Lys Phe Phe Lys Ala Tyr Ser Ala Lys Glu
        275                 280                 285
Lys Glu Asn Ile Arg Gln Glu Ile Ser Ile Met Asn Cys Leu His His
    290                 295                 300
Pro Lys Leu Val Gln Cys Val Asp Ala Phe Glu Glu Lys Ala Asn Ile
305                 310                 315                 320
Val Met Val Leu Glu Ile Val Ser Gly Gly Glu Leu Phe Glu Arg Ile
                325                 330                 335
Ile Asp Glu Asp Phe Glu Leu Thr Glu Arg Glu Cys Ile Lys Tyr Met
            340                 345                 350
Arg Gln Ile Ser Glu Gly Val Glu Tyr Ile His Lys Gln Gly Ile Val
        355                 360                 365
His Leu Asp Leu Lys Pro Glu Asn Ile Met Cys Val Asn Lys Thr Gly
    370                 375                 380
Thr Arg Ile Lys Leu Ile Asp Phe Gly Leu Ala Arg Arg Leu Glu Asn
385                 390                 395                 400
Ala Gly Ser Leu Lys Val Leu Phe Gly Thr Pro Glu Phe Val Ala Pro
                405                 410                 415
Glu Val Ile Asn Tyr Glu Pro Ile Ser Tyr Ala Thr Asp Met Trp Ser
            420                 425                 430
Ile Gly Val Ile Cys Tyr Ile Leu Val Ser Gly Leu Ser Pro Phe Met
        435                 440                 445
Gly Asp Asn Asp Asn Glu Thr Leu Ala Asn Val Thr Ser Ala Thr Trp
    450                 455                 460
Asp Phe Asp Asp Glu Ala Phe Asp Glu Ile Ser Asp Asp Ala Lys Asp
465                 470                 475                 480
Phe Ile Ser Asn Leu Leu Lys Lys Asp Met Lys Asn Arg Leu Asp Cys
                485                 490                 495
Thr Gln Cys Leu Gln His Pro Trp Leu Met Lys Asp
            500                 505
```

<210> SEQ ID NO 20
<211> LENGTH: 106
<212> TYPE: PRT
<213> ORGANISM: Human

<400> SEQUENCE: 20

```
Pro Tyr Phe Ser Lys Thr Ile Arg Asp Leu Glu Val Val Glu Gly Ser
1               5                   10                  15
Ala Ala Arg Phe Asp Cys Lys Ile Glu Gly Tyr Pro Asp Pro Glu Val
            20                  25                  30
Val Trp Phe Lys Asp Asp Gln Ser Ile Arg Glu Ser Arg His Phe Gln
        35                  40                  45
```

-continued

```
Ile Asp Tyr Asp Glu Asp Gly Asn Cys Ser Leu Ile Ile Ser Asp Val
    50                  55                  60
Cys Gly Asp Asp Ala Lys Tyr Thr Cys Lys Ala Val Asn Ser Leu
65                  70                  75                  80
Gly Glu Ala Thr Cys Thr Ala Glu Leu Ile Val Glu Thr Met Glu Glu
                85                  90                  95
Gly Glu Gly Glu Gly Glu Glu Glu Glu
            100                 105
```

<210> SEQ ID NO 21
<211> LENGTH: 96
<212> TYPE: PRT
<213> ORGANISM: Human

<400> SEQUENCE: 21

```
Pro Pro Lys Phe Ala Thr Lys Leu Gly Arg Val Val Lys Glu Gly
1               5                   10                  15
Gln Met Gly Arg Phe Ser Cys Lys Ile Thr Gly Arg Pro Gln Pro Gln
                20                  25                  30
Val Thr Trp Leu Lys Gly Asn Val Pro Leu Gln Pro Ser Ala Arg Val
            35                  40                  45
Ser Val Ser Glu Lys Asn Gly Met Gln Val Leu Glu Ile His Gly Val
    50                  55                  60
Asn Gln Asp Asp Val Gly Val Tyr Thr Cys Leu Val Asn Gly Ser
65                  70                  75                  80
Gly Lys Ala Ser Met Ser Ala Glu Leu Ser Ile Gln Gly Leu Asp Ser
                85                  90                  95
```

<210> SEQ ID NO 22
<211> LENGTH: 96
<212> TYPE: PRT
<213> ORGANISM: Human

<400> SEQUENCE: 22

```
Pro Pro Lys Phe Ala Thr Lys Leu Gly Arg Val Val Lys Glu Gly
1               5                   10                  15
Gln Met Gly Arg Phe Ser Cys Lys Ile Thr Gly Arg Pro Gln Pro Gln
                20                  25                  30
Val Thr Trp Leu Lys Gly Asn Val Pro Leu Gln Pro Ser Ala Arg Val
            35                  40                  45
Ser Val Ser Glu Lys Asn Gly Met Gln Val Leu Glu Ile His Gly Val
    50                  55                  60
Asn Gln Asp Asp Val Gly Val Tyr Thr Cys Leu Val Asn Gly Ser
65                  70                  75                  80
Gly Lys Ala Ser Met Ser Ala Glu Leu Ser Ile Gln Gly Leu Asp Ser
                85                  90                  95
```

<210> SEQ ID NO 23
<211> LENGTH: 88
<212> TYPE: PRT
<213> ORGANISM: Human

<400> SEQUENCE: 23

```
Pro Lys Phe Ala Thr Lys Leu Gly Arg Val Val Lys Glu Gly Gln
1               5                   10                  15
Met Gly Arg Phe Ser Cys Lys Ile Thr Gly Arg Pro Gln Pro Gln Val
                20                  25                  30
Thr Trp Leu Lys Gly Asn Val Pro Leu Gln Pro Ser Ala Arg Val Ser
```

```
                35                  40                  45
Val Ser Glu Lys Asn Gly Met Gln Val Leu Glu Ile His Gly Val Asn
         50                  55                  60
Gln Asp Asp Val Gly Val Tyr Thr Cys Leu Val Val Asn Gly Ser Gly
 65                  70                  75                  80
Lys Ala Ser Met Ser Ala Glu Leu
                 85

<210> SEQ ID NO 24
<211> LENGTH: 94
<212> TYPE: PRT
<213> ORGANISM: Human

<400> SEQUENCE: 24

Ala Pro Ser Phe Ser Ser Val Leu Lys Asp Cys Ala Val Ile Glu Gly
  1               5                  10                  15
Gln Asp Phe Val Leu Gln Cys Ser Val Arg Gly Thr Pro Val Pro Arg
                 20                  25                  30
Ile Thr Trp Leu Leu Asn Gly Gln Pro Ile Gln Tyr Ala Arg Ser Thr
             35                  40                  45
Cys Glu Ala Gly Val Ala Glu Leu His Ile Gln Asp Ala Leu Pro Glu
         50                  55                  60
Asp His Gly Thr Tyr Thr Cys Leu Ala Glu Asn Ala Leu Gly Gln Val
 65                  70                  75                  80
Ser Cys Ser Ala Trp Val Thr His Glu Lys Lys Ser Ser
                 85                  90

<210> SEQ ID NO 25
<211> LENGTH: 112
<212> TYPE: PRT
<213> ORGANISM: Human

<400> SEQUENCE: 25

Lys Lys Ser Ser Arg Lys Ser Glu Tyr Leu Leu Pro Val Ala Pro Ser
  1               5                  10                  15
Lys Pro Thr Ala Pro Ile Phe Leu Gln Gly Leu Ser Asp Leu Lys Val
                 20                  25                  30
Met Asp Gly Ser Gln Val Thr Met Thr Val Gln Val Ser Gly Asn Pro
             35                  40                  45
Pro Pro Glu Val Ile Trp Leu His Asn Gly Asn Glu Ile Gln Glu Ser
         50                  55                  60
Glu Asp Phe His Phe Glu Gln Arg Gly Thr Gln His Ser Leu Trp Ile
 65                  70                  75                  80
Gln Glu Val Phe Pro Glu Asp Thr Gly Thr Tyr Thr Cys Glu Ala Trp
                 85                  90                  95
Asn Ser Ala Gly Glu Val Arg Thr Gln Ala Val Leu Thr Val Gln Glu
                100                 105                 110

<210> SEQ ID NO 26
<211> LENGTH: 100
<212> TYPE: PRT
<213> ORGANISM: Human

<400> SEQUENCE: 26

Ser Met Pro Leu Thr Glu Ala Pro Ala Phe Ile Leu Pro Pro Arg Asn
  1               5                  10                  15
Leu Cys Ile Lys Glu Gly Ala Thr Ala Lys Phe Glu Gly Arg Val Arg
                 20                  25                  30
```

```
Gly Tyr Pro Glu Pro Gln Val Thr Trp His Arg Asn Gly Gln Pro Ile
            35                  40                  45

Thr Ser Gly Gly Arg Phe Leu Leu Asp Cys Gly Ile Arg Gly Thr Phe
 50                      55                  60

Ser Leu Val Ile His Ala Val His Glu Glu Asp Arg Gly Lys Tyr Thr
 65                  70                  75                  80

Cys Glu Ala Thr Asn Gly Ser Gly Ala Arg Gln Val Thr Val Glu Leu
                 85                  90                  95

Thr Val Glu Gly
            100

<210> SEQ ID NO 27
<211> LENGTH: 174
<212> TYPE: PRT
<213> ORGANISM: Human

<400> SEQUENCE: 27

Pro Ser Gly Glu Glu Arg Lys Arg Pro Ala Pro Pro Arg Pro Ala Thr
 1               5                  10                  15

Phe Pro Thr Arg Gln Pro Gly Leu Gly Ser Gln Asp Val Val Ser Lys
                 20                  25                  30

Ala Ala Asn Arg Arg Ile Pro Met Glu Gly Gln Arg Asp Ser Ala Phe
             35                  40                  45

Pro Lys Phe Glu Ser Lys Pro Gln Ser Gln Glu Val Lys Glu Asn Gln
 50                      55                  60

Thr Val Lys Phe Arg Cys Glu Val Ser Gly Ile Pro Lys Pro Glu Val
 65                  70                  75                  80

Ala Trp Phe Leu Glu Gly Thr Pro Val Arg Arg Gln Glu Gly Ser Ile
                 85                  90                  95

Glu Val Tyr Glu Asp Ala Gly Ser His Tyr Leu Cys Leu Leu Lys Ala
            100                 105                 110

Arg Thr Arg Asp Ser Gly Thr Tyr Ser Cys Thr Ala Ser Asn Ala Gln
        115                 120                 125

Gly Gln Val Ser Cys Ser Trp Thr Leu Gln Val Glu Arg Leu Ala Val
    130                 135                 140

Met Glu Val Ala Pro Ser Phe Ser Val Leu Lys Asp Cys Ala Val
145                 150                 155                 160

Ile Glu Gly Gln Asp Phe Val Leu Gln Cys Ser Val Arg Gly
                165                 170

<210> SEQ ID NO 28
<211> LENGTH: 97
<212> TYPE: PRT
<213> ORGANISM: Human

<400> SEQUENCE: 28

Pro Ala Phe Lys Gln Lys Leu Gln Asp Val His Val Ala Glu Gly Lys
 1               5                  10                  15

Lys Leu Leu Leu Gln Cys Gln Val Ser Ser Asp Pro Pro Ala Thr Ile
                 20                  25                  30

Ile Trp Thr Leu Asn Gly Lys Thr Leu Lys Thr Thr Lys Phe Ile Ile
             35                  40                  45

Leu Ser Gln Glu Gly Ser Leu Cys Ser Val Ser Ile Glu Lys Ala Leu
 50                      55                  60

Leu Glu Asp Arg Gly Leu Tyr Lys Cys Val Ala Lys Asn Asp Ala Gly
 65                  70                  75                  80
```

```
Gln Ala Glu Cys Ser Cys Gln Val Thr Val Asp Asp Ala Pro Ala Ser
                85                  90                  95

Glu

<210> SEQ ID NO 29
<211> LENGTH: 124
<212> TYPE: PRT
<213> ORGANISM: Human

<400> SEQUENCE: 29

Glu Ser Gln Gly Thr Ala Pro Ala Phe Lys Gln Lys Leu Gln Asp Val
  1               5                  10                  15

His Val Ala Glu Gly Lys Lys Leu Leu Leu Gln Cys Gln Val Ser Ser
                20                  25                  30

Asp Pro Pro Ala Thr Ile Ile Trp Thr Leu Asn Gly Lys Thr Leu Lys
                35                  40                  45

Thr Thr Lys Phe Ile Ile Leu Ser Gln Glu Gly Ser Leu Cys Ser Val
            50                  55                  60

Ser Ile Glu Lys Ala Leu Leu Glu Asp Arg Gly Leu Tyr Lys Cys Val
 65                  70                  75                  80

Ala Lys Asn Asp Ala Gly Gln Ala Glu Cys Ser Cys Gln Val Thr Val
                85                  90                  95

Asp Asp Ala Pro Ala Ser Glu Asn Thr Lys Ala Pro Glu Met Lys Ser
               100                 105                 110

Arg Arg Pro Lys Ser Ser Leu Pro Pro Val Leu Gly
               115                 120

<210> SEQ ID NO 30
<211> LENGTH: 87
<212> TYPE: PRT
<213> ORGANISM: Human

<400> SEQUENCE: 30

Ala Pro Ala Phe Ile Leu Pro Pro Arg Asn Leu Cys Ile Lys Glu Gly
  1               5                  10                  15

Ala Thr Ala Lys Phe Glu Gly Arg Val Arg Gly Tyr Pro Glu Pro Gln
                20                  25                  30

Val Thr Trp His Arg Asn Gly Gln Pro Ile Thr Ser Gly Gly Arg Phe
                35                  40                  45

Leu Leu Asp Cys Gly Ile Arg Gly Thr Phe Ser Leu Val Ile His Ala
            50                  55                  60

Val His Glu Glu Asp Arg Gly Lys Tyr Thr Cys Glu Ala Thr Asn Gly
 65                  70                  75                  80

Ser Gly Ala Arg Gln Val Thr
                85

<210> SEQ ID NO 31
<211> LENGTH: 119
<212> TYPE: PRT
<213> ORGANISM: Human

<400> SEQUENCE: 31

Ser Asn Ala Gln Gly Gln Val Ser Cys Ser Trp Thr Leu Gln Val Glu
  1               5                  10                  15

Arg Leu Ala Val Met Glu Val Ala Pro Ser Phe Ser Val Leu Lys
                20                  25                  30

Asp Cys Ala Val Ile Glu Gly Gln Asp Phe Val Leu Gln Cys Ser Val
```

-continued

```
                35                  40                  45
Arg Gly Thr Pro Val Pro Arg Ile Thr Trp Leu Leu Asn Gly Gln Pro
     50                  55                  60
Ile Gln Tyr Ala Arg Ser Thr Cys Glu Ala Gly Val Ala Glu Leu His
 65                  70                  75                  80
Ile Gln Asp Ala Leu Pro Glu Asp His Gly Thr Tyr Thr Cys Leu Ala
                 85                  90                  95
Glu Asn Ala Leu Gly Gln Val Ser Cys Ser Ala Trp Val Thr Val His
                100                 105                 110
Glu Lys Lys Ser Ser Arg Lys
                115

<210> SEQ ID NO 32
<211> LENGTH: 98
<212> TYPE: PRT
<213> ORGANISM: Human

<400> SEQUENCE: 32

Gly Gln Arg Asp Ser Ala Phe Pro Lys Phe Glu Ser Lys Pro Gln Ser
  1               5                  10                  15
Gln Glu Val Lys Glu Asn Gln Thr Val Lys Phe Arg Cys Glu Val Ser
                 20                  25                  30
Gly Ile Pro Lys Pro Glu Val Ala Trp Phe Leu Glu Gly Thr Pro Val
                 35                  40                  45
Arg Arg Gln Glu Gly Ser Ile Glu Val Tyr Glu Asp Ala Gly Ser His
     50                  55                  60
Tyr Leu Cys Leu Leu Lys Ala Arg Thr Arg Asp Ser Gly Thr Tyr Ser
 65                  70                  75                  80
Cys Thr Ala Ser Asn Ala Gln Gly Gln Val Ser Cys Ser Trp Thr Leu
                 85                  90                  95
Gln Val

<210> SEQ ID NO 33
<211> LENGTH: 82
<212> TYPE: PRT
<213> ORGANISM: Human

<400> SEQUENCE: 33

Val Thr Ala Ser Leu Gly Gln Ser Val Leu Ile Ser Cys Ala Ile Ala
  1               5                  10                  15
Gly Asp Pro Phe Pro Thr Val His Trp Leu Arg Asp Gly Lys Ala Leu
                 20                  25                  30
Cys Lys Asp Thr Gly His Phe Glu Val Leu Gln Asn Glu Asp Val Phe
                 35                  40                  45
Thr Leu Val Leu Lys Lys Val Gln Pro Trp His Ala Gly Gln Tyr Glu
     50                  55                  60
Ile Leu Leu Lys Asn Arg Val Gly Glu Cys Ser Cys Gln Val Ser Leu
 65                  70                  75                  80
Met Leu

<210> SEQ ID NO 34
<211> LENGTH: 89
<212> TYPE: PRT
<213> ORGANISM: Human

<400> SEQUENCE: 34

Pro Tyr Phe Ser Lys Thr Ile Arg Asp Leu Glu Val Val Glu Gly Ser
```

-continued

```
1               5                    10                   15
Ala Ala Arg Phe Asp Cys Lys Ile Glu Gly Tyr Pro Asp Pro Glu Val
            20                  25              30
Val Trp Phe Lys Asp Asp Gln Ser Ile Arg Glu Ser Arg His Phe Gln
        35                  40              45
Ile Asp Tyr Asp Glu Asp Gly Asn Cys Ser Leu Ile Ile Ser Asp Val
    50                  55              60
Cys Gly Asp Asp Asp Ala Lys Tyr Thr Cys Lys Ala Val Asn Ser Leu
65                  70                  75                  80
Gly Glu Ala Thr Cys Thr Ala Glu Leu
                85
```

ISOLATED HUMAN KINASE PROTEINS

RELATED APPLICATIONS

The present application is a divisional of U.S. application Ser. No. 09/858,664, filed on May 17, 2001 and issued on Nov. 19, 2002 as U.S. Pat. No. 6,482,624, which is a continuation-in-part of U.S. Application Ser. No. 09/711,134, filed on Nov. 14, 2000 now abandoned.

FIELD OF THE INVENTION

The present invention is in the field of kinase proteins that are related to the myosin light chain kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Myosin Light Chain Kinase

Activation of smooth/nonmuscle myosin light chain kinase (MLCK) by Ca/calmodulin results in phosphorylation of myosin regulatory light chain that plays important roles in initiation of smooth muscle contraction, endothelial cell retraction, secretion, and other cellular processes (Stull et al., in *International Symposium on Regulation of the Contractile Cycle in Smooth Muscle*, Apr. 26, 1995, Mie, Japan). The same myosin light chain kinases are present in smooth and nonmuscle tissues. (Gallagher et al., *J Biol Chem Dec.* 15, 1991;266(35):23936–44, Published erratum appears in *J Biol Chem May* 5, 1992;267(13):9450). The phosphorylation of myosin light chains by myosin light chain kinase is a key event in agonist-mediated endothelial cell gap formation and vascular permeability. Amino acid sequence analysis indicates endothelial MLCK consensus sequences for a variety of protein kinases including highly conserved potential phosphorylation sites for cAMP-dependent protein kinase A (PKA) in the CaM-binding region. Augmentation of intracellular cAMP levels markedly enhanced MLCK phosphorylation (2.5-fold increase) and reduced kinase activity in MLCK immunoprecipitates (4-fold decreases) (Garcia et al., *Am J Respir Cell Mol Biol* May 1997;16(5):489–94). The smooth/nonmuscle myosin light chain kinase contains a catalytic core homologous to that of other protein kinases and a carboxyl-terminal regulatory domain consisting of both an inhibitory sequence and a calmodulin-binding sequence (Kemp et al., *Trends Biochem. Sci.* 19, 440–444, 1994; Stull et al., 1995). Initially, inspection of the linear sequence within the regulatory domain revealed a similar number and sequential arrangement of 4 basic residues with those shown to be important substrate determinants in a synthetic peptide containing residues 11–23 of the myosin regulatory light chain. Thus, it has been proposed that the regulatory domain contained a pseudosubstrate inhibitory sequence whereby 4 specific basic residues in myosin light chain kinase mimic the basic substrate determinants in the light chain peptide substrate. Binding of the pseudosubstrate sequence to the active site inhibited activity. Intrasteric inhibition involves an autoinhibitory sequence that folds back on the catalytic site to inhibit kinase activity as opposed to an allosteric mechanism whereby a conformational change induced at a site distinct from the active site would be responsible for regulation of enzyme activity (Kemp et al., *Biochim. Biophys. Acta.* 1094, 67–76, 1991). The sequence comprising the pseudosubstrate region was later expanded to include overlap with the complete amino terminus of the light chain (Faux et al., *Mol. Cell. Biochem.* 128, 81–91, 1993). However, these additional residues(1, 2, 3, 4, 5, 6, 7, 8, 9, 10) are not important for substrate binding and thus are not part of the consensus phosphorylation sequence (Kemp et al., *Trends Biochem. Sci.* 15, 342–346, 1990).

Kinase proteins, particularly members of the myosin light chain kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the myosin light chain kinase subfamily.

SUMMARY OF THE INVENTION

The present invention is based in part on the identification of amino acid sequences of human kinase peptides and proteins that are related to the myosin light chain kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the human placenta, kidney, lung, skeletal muscle, heart, fetal brain, and colon carcinoma.

DESCRIPTION OF THE FIGURE SHEETS

FIGS. 1A–1B provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the human placenta, kidney, lung, skeletal muscle, heart, fetal brain, and colon carcinoma.

FIGS. 2A–2L provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3C provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. 6 SNPs, have been identified in the gene encoding the kinase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the myosin light chain kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the myosin light chain kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the myosin light chain kinase subfamily and the expression pattern observed. Experimental data as provided in FIG. 1 indicates expression in the human placenta, kidney, lung, skeletal muscle, heart, fetal brain, and colon carcinoma. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known myosin light chain kinase family or subfamily of kinase proteins.

Specific Embodiments

Peptide Molecules

The present invention provides nucleic acid sequences that encode protein molecules that have been identified as being members of the kinase family of proteins and are related to the myosin light chain kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the human placenta, kidney, lung, skeletal muscle, heart, fetal brain, and colon carcinoma. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 1 by ePCR, and confirmed with radiation hybrid mapping. As indicated by the data presented in FIG. 3, the gene provided by the present invention encoding a novel phosphatase maps to public BAC AC AC023889, which is known to be located on human chromosome 1.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 1 by ePCR, and confirmed with radiation hybrid mapping. As indicated by the data presented in FIG. 3, the gene provided by the present invention encoding a novel phosphatase maps to public BAC AC AC023889, which is known to be located on human chromosome 1. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been identified in a gene encoding the kinase protein of the present invention. 6 SNP variants were found, and all SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Substantial chemical and structural homology exists between the kinase protein of the present invention described herein and myosin light chain kinase (see FIG. 1). As discussed in the background, myosin light chain kinase are known in the art to be involved in smooth muscle contraction, endothelial cell retraction, secretion, and other cellular process. Accordingly, the myosin light chain kinase, and the encoding gene, provided by the present invention is useful for treating, preventing, and/or diagnosing disorders associated with muscle, endothelial cells.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain. A large percentage of pharmaceutical agents are being developed that modulate the activity of kinase proteins, particularly members of the myosin light chain kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the human placenta, kidney, lung, skeletal muscle, heart, fetal brain, and colon carcinoma. Such uses can readily be determined using the information provided herein, that which is known in the art, and routine experimentation.

The proteins of the present invention (including variants and fragments that may have been disclosed prior to the present invention) are useful for biological assays related to kinases that are related to members of the myosin light chain kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the human placenta, kidney, lung, skeletal muscle, heart, fetal brain, and colon carcinoma. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the human placenta, kidney, lung, skeletal muscle, heart, fetal brain, and colon carcinoma. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide.

Accordingly, the invention provides methods for detecting the presence, or levels of, the protein (or encoding mRNA) in a cell, tissue, or organism. Experimental data as provided in FIG. 1 indicates expression in the human placenta, kidney, lung, skeletal muscle, heart, fetal brain, and colon carcinoma. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, inmmunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the human placenta, kidney, lung, skeletal muscle, heart, fetal brain, and colon carcinoma. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the human placenta, kidney, lung, skeletal muscle, heart, fetal brain, and colon carcinoma. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the human placenta, kidney, lung, skeletal muscle, heart, fetal brain, and colon carcinoma. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the human placenta, kidney, lung, skeletal muscle, heart, fetal brain, and colon carcinoma. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 1 by ePCR, and confirmed with radiation hybrid mapping. As indicated by the data presented in FIG. 3, the gene provided by the present invention encoding a novel phosphatase maps to public BAC AC AC023889, which is known to be located on human chromosome 1.

FIG. 3 provides information on SNPs that have been identified in a gene encoding the kinase protein of the present invention. 6 SNP variants were found, and all SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 6 SNPs, have been identified in the gene encoding the kinase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 1 by ePCR, and confirmed with radiation hybrid mapping. As indicated by the data presented in FIG. 3, the gene provided by the present invention encoding a novel phosphatase maps to public BAC AC AC023889, which is known to be located on human chromosome 1.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the human placenta, kidney, lung, skeletal muscle, heart, fetal brain, and colon carcinoma. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the human placenta, kidney, lung, skeletal muscle, heart, fetal brain, and colon carcinoma.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been identified in a gene encoding the kinase protein of the present invention. 6 SNP variants were found, and all SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference. As indicated by the data presented in FIG. 3, the map position was determined to be on chromosome 1 by ePCR, and confirmed with radiation hybrid mapping. As indicated by the data presented in FIG. 3, the gene provided by the present invention encoding a novel phosphatase maps to public BAC AC AC023889, which is known to be located on human chromosome 1. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been identified in a gene encoding the kinase protein of the present invention. 6 SNP variants were found, and all SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the human placenta, kidney, lung, skeletal muscle, heart, fetal brain, and colon carcinoma. Specifically, a virtual northern blot shows expression in human colon carcinoma. In addition, PCR-based tissue screening panel indicates expression in human placenta, kidney, lung, skeletal muscle, heart, and fetal brain. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been identified in a gene encoding the kinase protein of the present invention. 6 SNP variants were found, and all SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. PNAS 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.
2. An isolated polypeptide having an amino acid sequence comprising SEQ ID NO:2.
3. A composition comprising the polypeptide of claim 1 and a carrier.
4. A composition comprising the polypeptide of claim 2 and a carrier.
5. The isolated polypeptide of claim 1, except that residue 68 of SEQ ID NO:2 is valine.
6. The isolated polypeptide of claim 2, except that residue 68 of SEQ ID NO:2 is valine.
7. The isolated polypeptide of claim 1, except that residue 68 of SEQ ID NQ:2 is alanine.
8. The isolated polypeptide of claim 2, except that residue 68 of SEQ ID NO:2 is alanine.
9. The isolated polypeptide of claim 1, except that residue 545 of SEQ ID NO:2 is serine.
10. The isolated polypeptide of claim 2, except that residue 545 of SEQ ID NO:2 is serine.
11. The isolated polypeptide of claim 1, except that residue 869 of SEQ ID NO:2 is alanine.
12. The isolated polypeptide of claim 2, except that residue 869 of SEQ ID NO:2 is alanine.
13. A composition comprising the polypeptide of claim 5 and a carrier.
14. A composition comprising the polypeptide of claim 6 and a carrier.
15. A composition comprising the polypeptide of claim 7 and a carrier.
16. A composition comprising the polypeptide of claim 8 and a carrier.
17. A composition comprising the polypeptide of claim 9 and a carrier.
18. A composition comprising the polypeptide of claim 10 and a carrier.
19. A composition comprising the polypeptide of claim 11 and a carrier.
20. A composition comprising the polypeptide of claim 12 and a carrier.

* * * * *